(12) United States Patent
Yen

(10) Patent No.: US 10,312,451 B2
(45) Date of Patent: Jun. 4, 2019

(54) COMPOUND FOR ORGANIC ELECTROLUMINESCENT DEVICE

(71) Applicant: LUMINESCENCE TECHNOLOGY CORPORATION, Hsin-Chu (TW)

(72) Inventor: Feng-Wen Yen, Taipei (TW)

(*) Notice: Subject to any disclaimer, the term of this patent is extended or adjusted under 35 U.S.C. 154(b) by 433 days.

(21) Appl. No.: 14/949,830

(22) Filed: Nov. 23, 2015

(65) Prior Publication Data

US 2016/0218293 A1    Jul. 28, 2016

Related U.S. Application Data

(63) Continuation-in-part of application No. 14/604,754, filed on Jan. 26, 2015.

(51) Int. Cl.
   *C09B 1/00*    (2006.01)
   *C07C 13/62*   (2006.01)
   (Continued)

(52) U.S. Cl.
   CPC .......... *H01L 51/0056* (2013.01); *C07C 13/62* (2013.01); *C09B 1/00* (2013.01); *C09B 57/00* (2013.01); *C09B 57/001* (2013.01); *H01L 51/0052* (2013.01); *H01L 51/0054* (2013.01); *H01L 51/0057* (2013.01); *H01L 51/0058* (2013.01); *H01L 51/0067* (2013.01); *H01L 51/0072* (2013.01); *H01L 51/0074* (2013.01); *H05B 33/20* (2013.01); *C07C 2603/24* (2017.05); *C07C 2603/26* (2017.05); *C07C 2603/48* (2017.05); *C07C 2603/50* (2017.05); *C07C 2603/54* (2017.05); *H01L 51/5004* (2013.01); *H01L 51/5012* (2013.01); *H01L 51/5016* (2013.01); *H01L 51/5072* (2013.01); *H01L 51/5076* (2013.01); *H01L 2251/5376* (2013.01); *H01L 2251/552* (2013.01)

(58) Field of Classification Search
   CPC ............ H01L 51/0056; H01L 51/0052; H01L 51/0057; H01L 51/0058; H01L 51/0072; H01L 51/0054; H01L 51/0067; H01L 51/0074; H01L 51/5076; H01L 51/5004; H01L 51/5016; H01L 51/5072; H01L 2251/5376; H01L 2251/552; H01L 51/5012; C09B 57/001; C09B 57/00; C09B 1/00; C07C 2603/54; C07C 2603/48; C07C 2603/50; C07C 2603/26; C07C 2603/24; C07C 13/62
   See application file for complete search history.

(56) References Cited

U.S. PATENT DOCUMENTS

| 8,962,160 B2 | 2/2015 | Yen et al. |
| 8,993,130 B2 | 3/2015 | Yen et al. |

(Continued)

FOREIGN PATENT DOCUMENTS

| KR | 2013007934 | * 12/2013 |
| WO | 2008062636 A1 | 5/2008 |
| WO | 2012091471 A2 | 7/2012 |

*Primary Examiner* — Kevin R Kruer

(57) ABSTRACT

The present invention generally discloses an organic compound and organic electroluminescence (herein referred to as organic EL) device using the organic compound. More specifically, the present invention relates to an organic EL device employing the organic compound as fluorescent emitting host or phosphorescent emitting host which can display long lifetime, high efficiency.

17 Claims, 1 Drawing Sheet

| 13 | — metal electrode |
| 12 | — electron injection layer |
| 11 | — electron transport layer |
| 10 | — hole blocking layer |
| 9  | — emitting layer |
| 8  | — hole transport layer |
| 7  | — hole injection layer |
| 6  | — transparent electrode |

(51) Int. Cl.
    *C09B 57/00*     (2006.01)
    *H01L 51/00*     (2006.01)
    *H01L 51/50*     (2006.01)
    *H05B 33/20*     (2006.01)

(56) References Cited

U.S. PATENT DOCUMENTS

| | | |
|---|---|---|
| 9,048,437 B2 | 6/2015 | Yen et al. |
| 2013/0048975 A1 | 2/2013 | Hong et al. |
| 2014/0151645 A1 | 6/2014 | Yen et al. |

\* cited by examiner

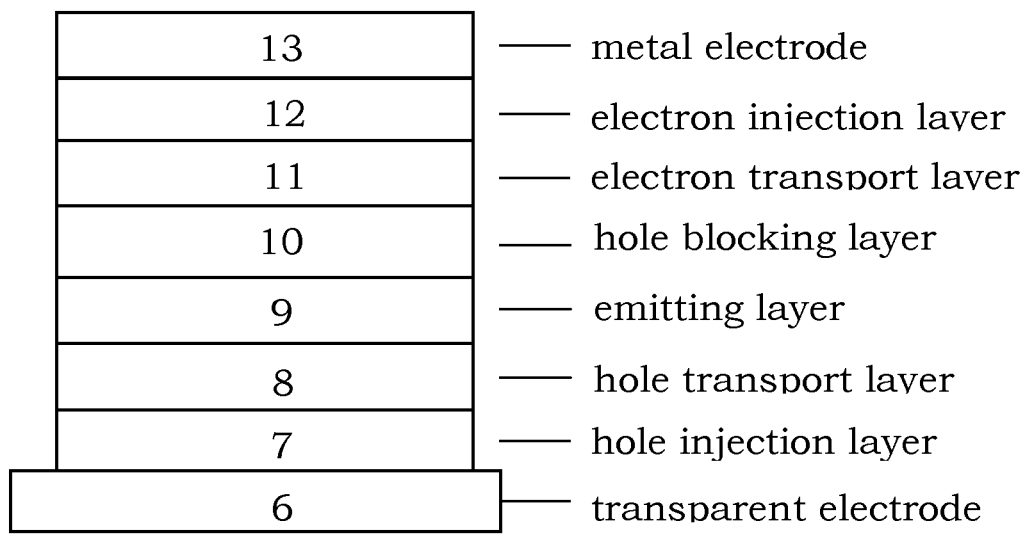

COMPOUND FOR ORGANIC ELECTROLUMINESCENT DEVICE

This application is a Continuation-in-Part of U.S. patent Ser. No. 14/604,754, filed Jan. 26, 2015.

FIELD OF INVENTION

The present invention generally relates to a compound and organic electroluminescent (herein referred to as organic EL) device using the compound. More specifically, the present invention relates to the compound having general formula(I), an organic EL device employing the compound as fluorescent emitting host or phosphorescent emitting host.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the phosphorescent emitting host material are also needed.

There continues to be a need for organic EL materials which is able to efficiently transport electrons or holes and block holes, with good thermal stability and more efficient EML material for high emitting efficiency. According to the reasons described above, the present invention has the objective of resolving such problems of the prior-art such as US20140131664A1, US20140175384A1 and US20140209866A1. The prior compounds used diaryl group linked to the position 12 of indenotriphenylene core. The present invention utilize a diaryl substituted arylene group linked to the position 5, 6, 7 and 8 of indenotriphenylene core and offering a light emitting device which is excellent in its thermal stability, high luminance efficiency, high luminance and long half-life time than the prior materials.

SUMMARY OF THE INVENTION

Provided a compound can use as fluorescent emitting host or phosphorescent emitting host for organic EL device. The compound can overcome the drawbacks of the prior materials such as US20140131664A1, US20140175384A1 and US20140209866A1 like as lower efficiency, half-lifetime and higher power consumption.

An object of the present invention is to provide the compound which can be used as fluorescent emitting host or phosphorescent emitting host for organic EL device.

The present invention has the economic advantages for industrial practice. Accordingly the present invention, the compound which can be used for organic EL device is disclosed. The mentioned the compound is represented by the following formula(I)

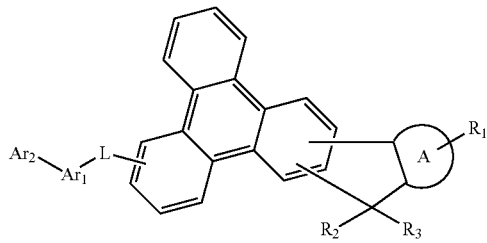

formula(I)

wherein A represents a phenyl group and a substituted or unsubstituted fused ring hydrocarbon units with two to four rings group, L represents a single bond or a substituted or unsubstituted divalent arylene group having 6 to 30 ring carbon atoms, $Ar_1$ and $Ar_2$ independently are selected from the group consisting of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group and a substituted or unsubstituted chrysenyl group; $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

BRIEF DESCRIPTION OF THE DRAWINGS

FIG. 1 show one example of organic EL device in the present invention. 6 is transparent electrode, 13 is metal electrode, 7 is hole injection layer which is deposited onto 6, 8 is hole transport layer which is deposited onto 7, 9 is fluorescent or phosphorescent emitting layer which is deposited onto 8, 10 is hole blocking layer which is deposited onto 9, 11 is electron transport layer which is deposited onto 10, 12 is electron injection layer which is deposited on to 11.

DESCRIPTION OF THE PREFERRED EMBODIMENTS

What probed into the invention is the compound and organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the compound which can be used as fluorescent emitting host or phosphorescent emitting host for organic EL device are disclosed. The mentioned compound are represented by the following formula(I)

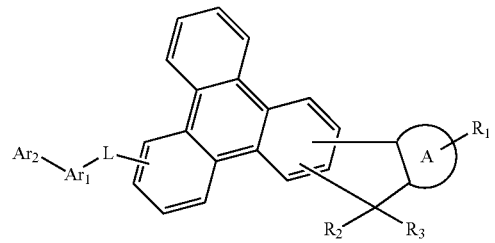

formula(I)

wherein A represents a phenyl group and a substituted or unsubstituted fused ring hydrocarbon units with two to four rings group, L represents a single bond or a substituted or unsubstituted divalent arylene group having 6 to 30 ring carbon atoms, $Ar_1$ and $Ar_2$ independently are selected from the group consisting of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group and a substituted or unsubstituted chrysenyl group; $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

According to the above-mentioned formula(I) wherein L is represented the following formulas:

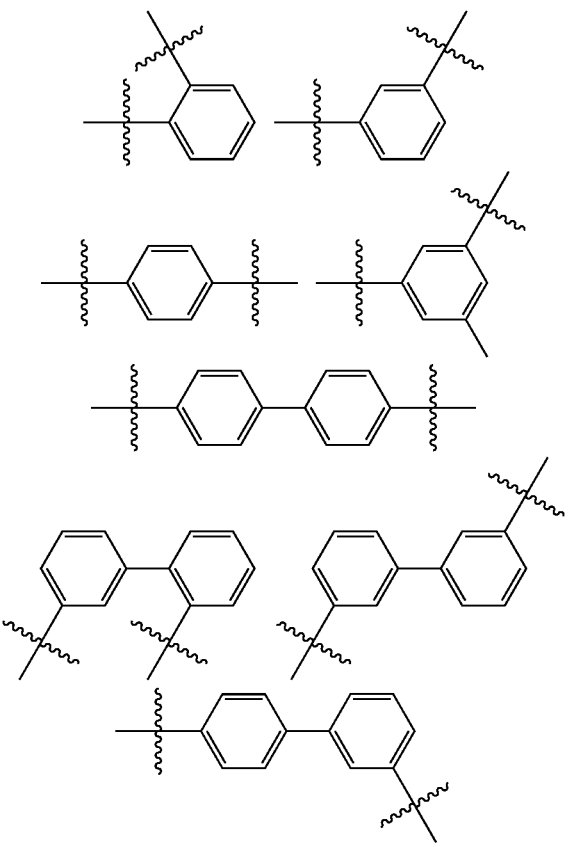

According to the above-mentioned formula(I) wherein Ar$_1$ is represented the following formulas:
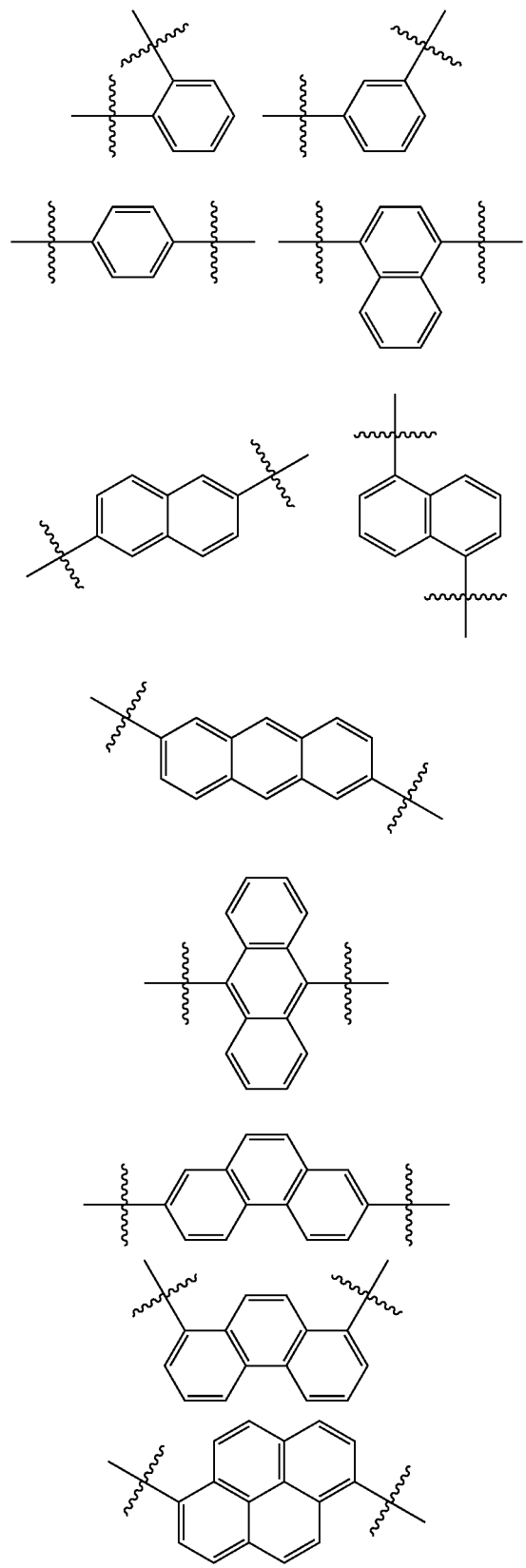
According to the above-mentioned formula(I) wherein Ar$_2$ is represented the following formulas:
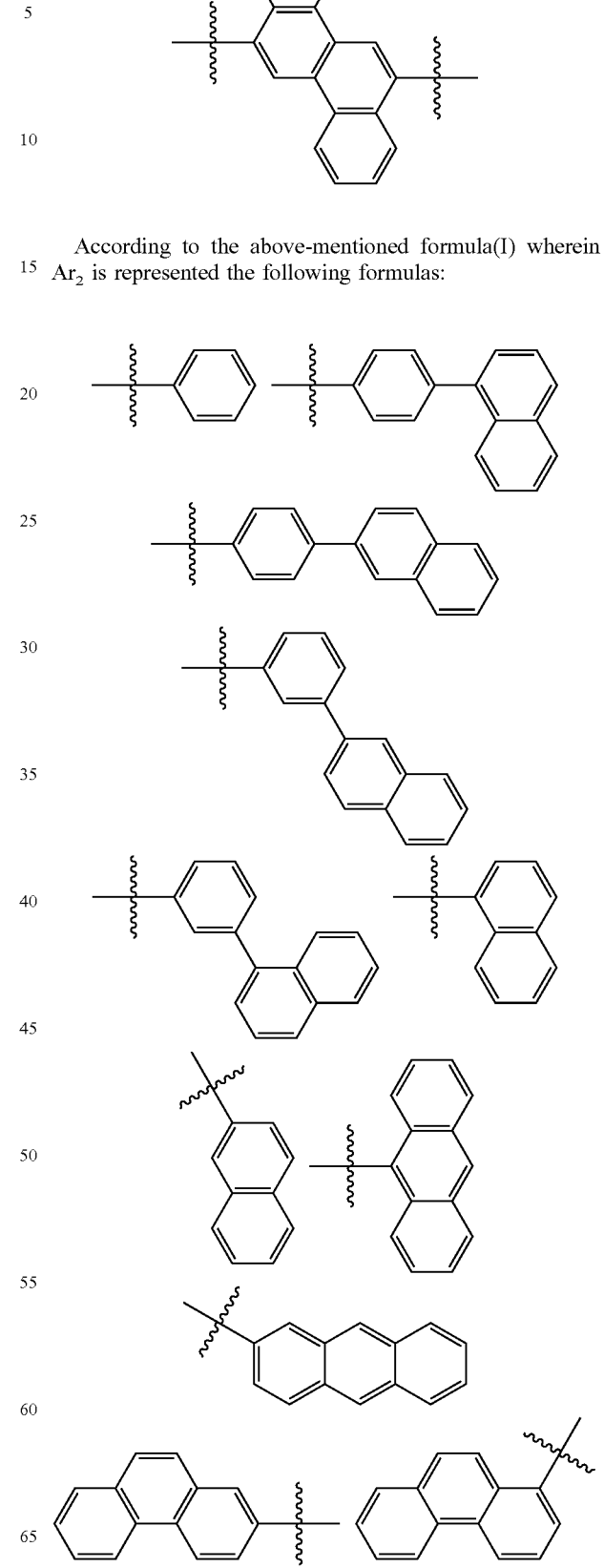

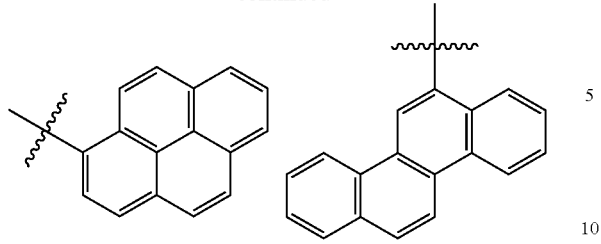

According to the above-mentioned the compound formula (I)) represented by the following formula(II) and formula (III):

formula(II)

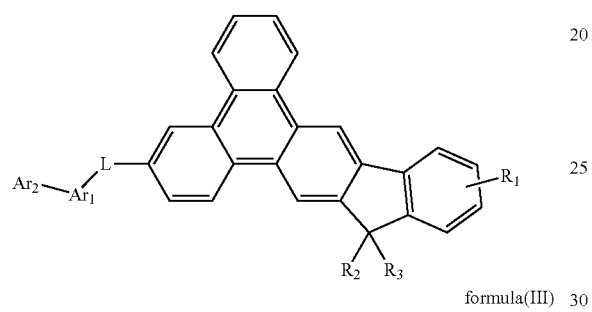

formula(III)

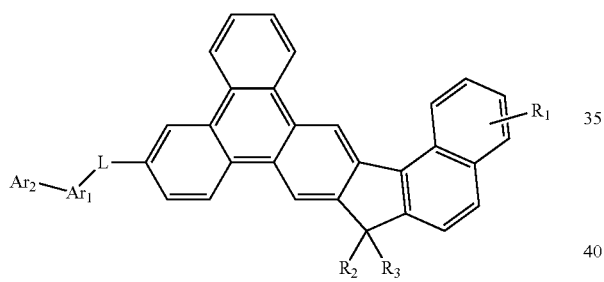

wherein L represents a single bond or a substituted or unsubstituted divalent arylene group having 6 to 30 ring carbon atoms, $Ar_1$ and $Ar_2$ independently are selected from the group consisting of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group and a substituted or unsubstituted chrysenyl group; $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

According to the above-mentioned compound formula(II) and formula(III), wherein the L is consisting of group represented as follows:

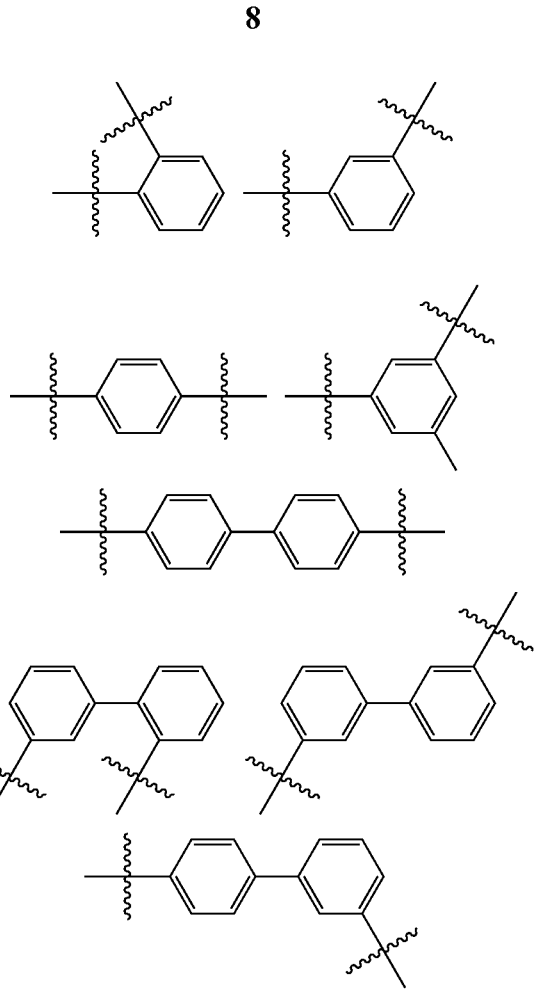

According to the above-mentioned compound formula(II) and formula(III), wherein the $Ar_1$ is consisting of group represented as follows:

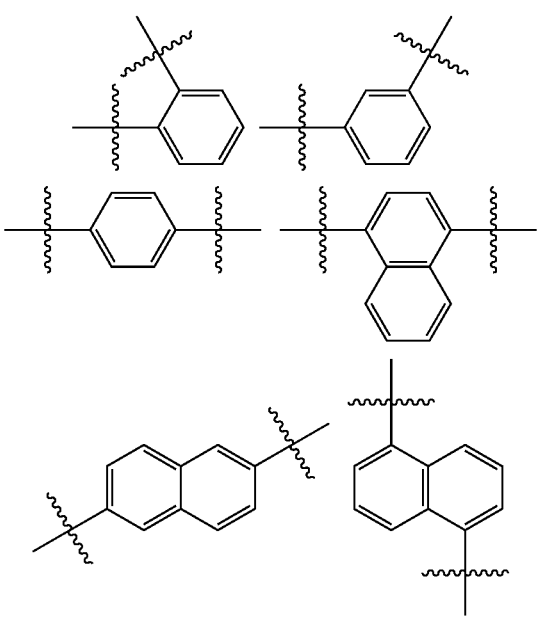

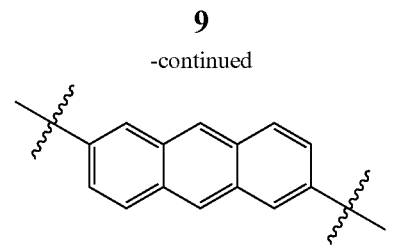
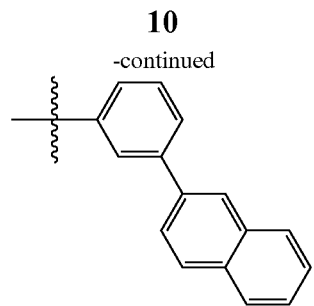
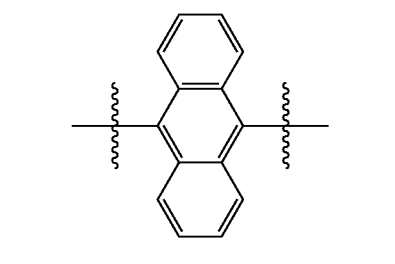
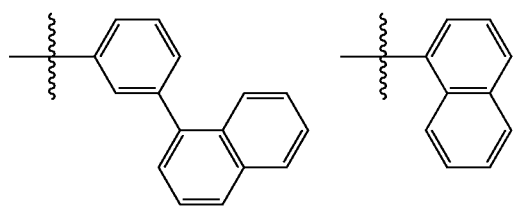
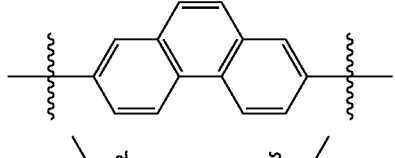
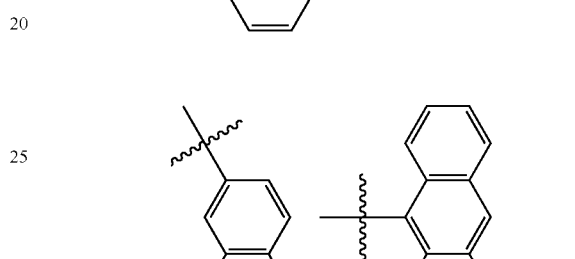
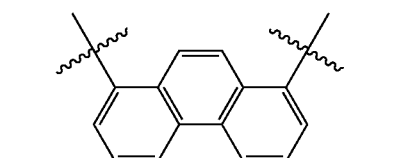
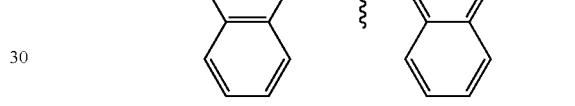
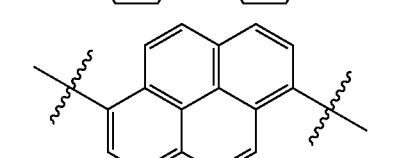
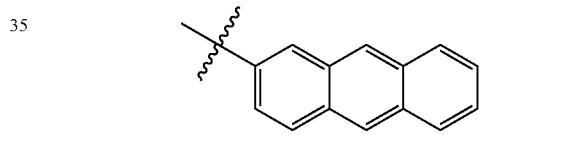
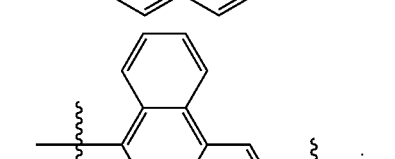
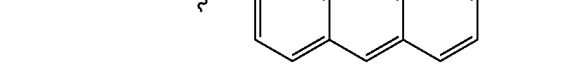
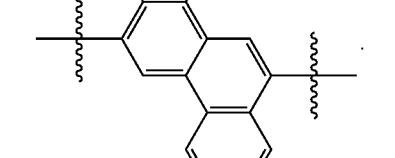
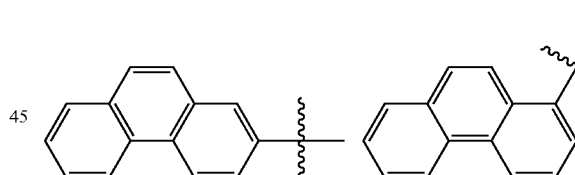
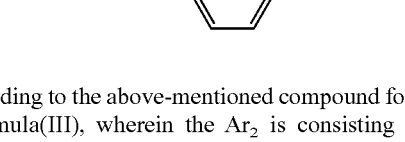
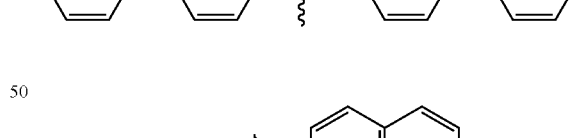
According to the above-mentioned compound formula(II) and formula(III), wherein the $Ar_2$ is consisting of group represented as follows:
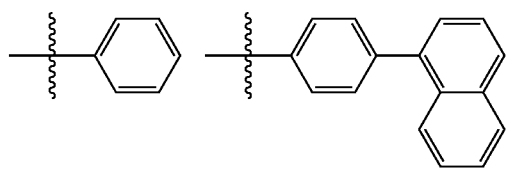
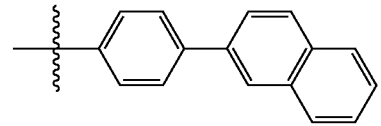
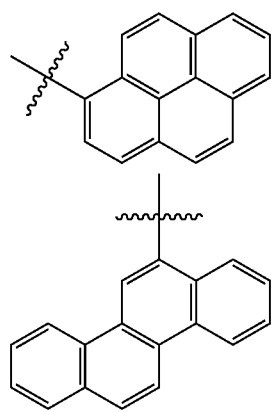

In this embodiment, some compounds are shown below:
EX1
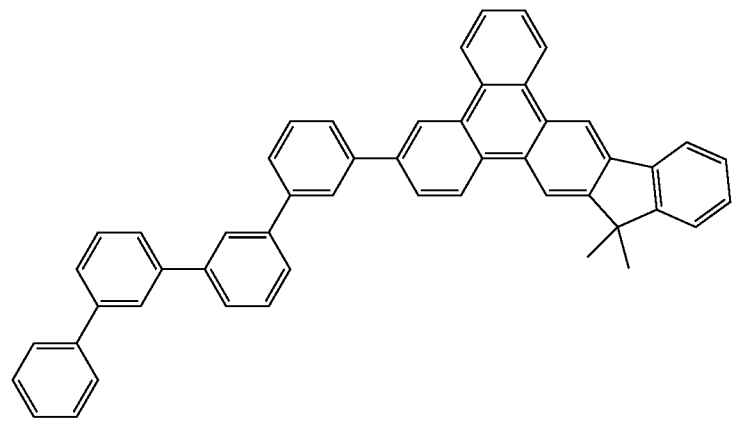
EX2
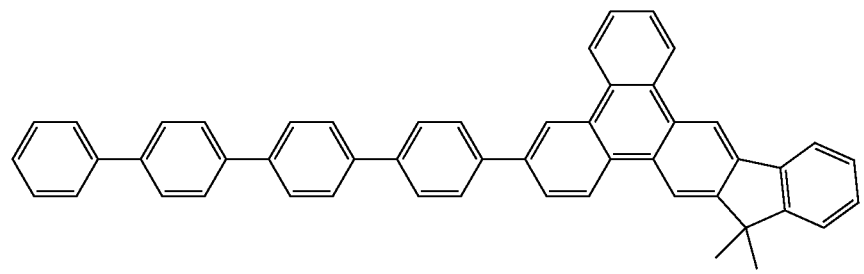
EX3 EX4
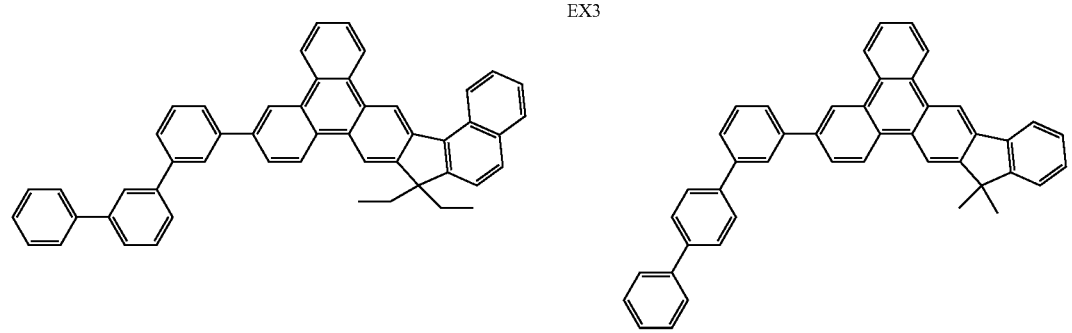
EX5 EX6
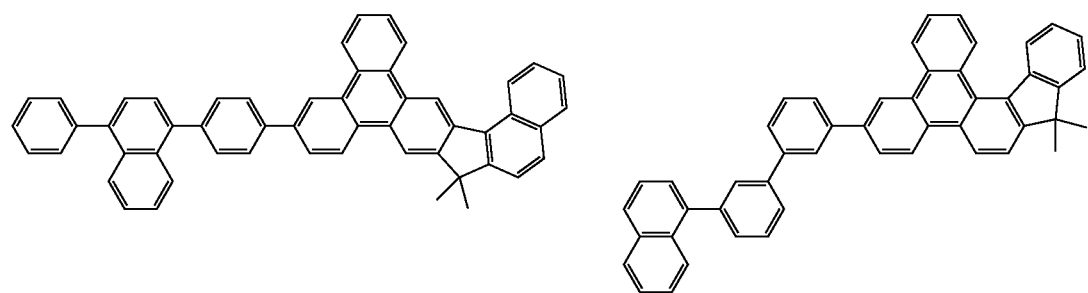
EX7
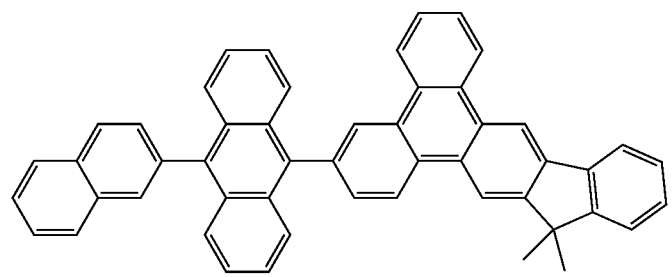

-continued
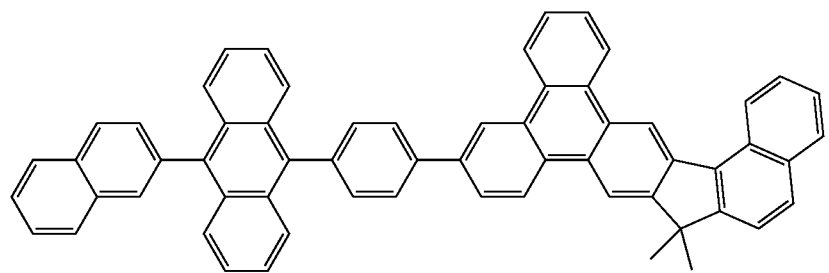
EX8
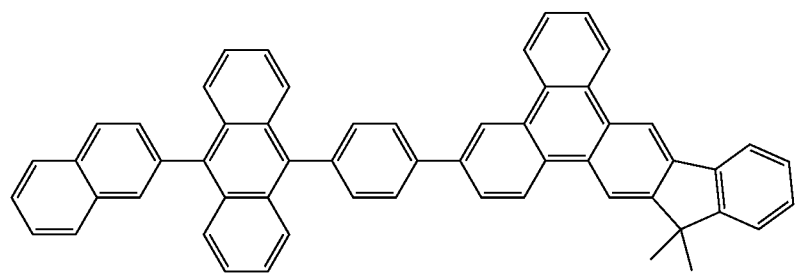
EX9
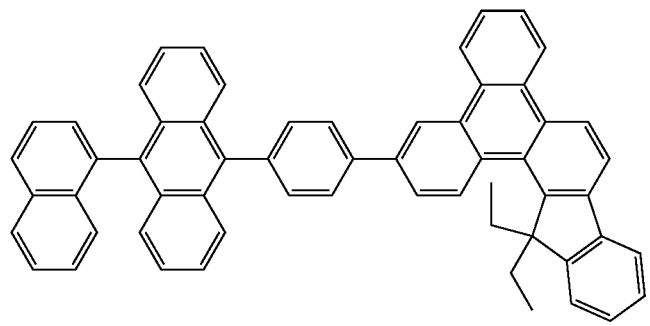
EX10
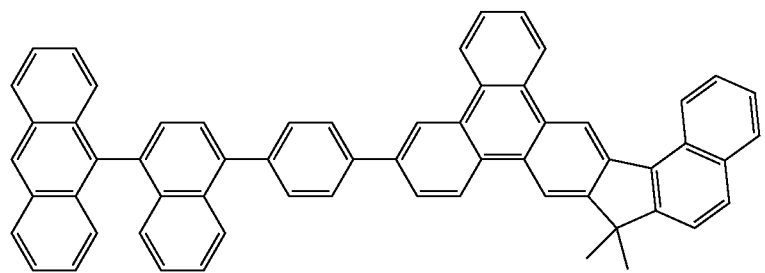
EX11
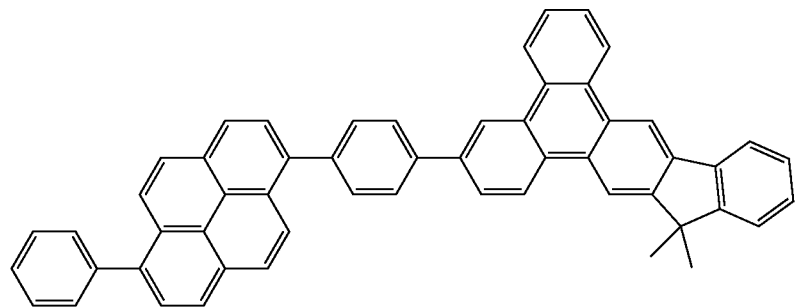
EX12

-continued
EX13
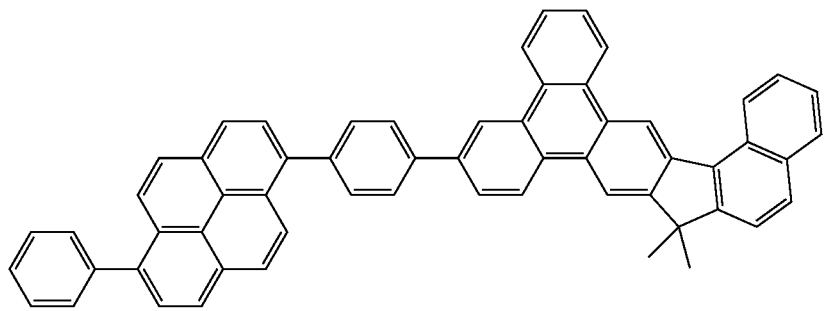
EX14
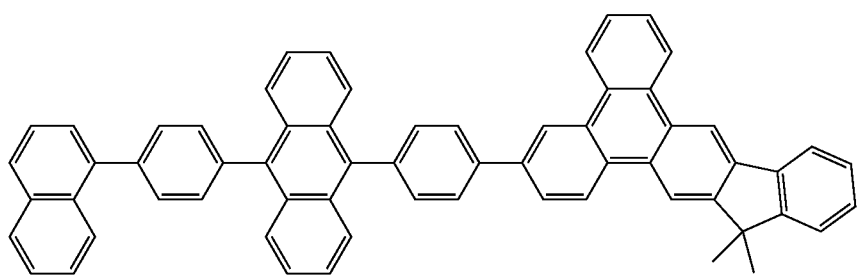
EX15
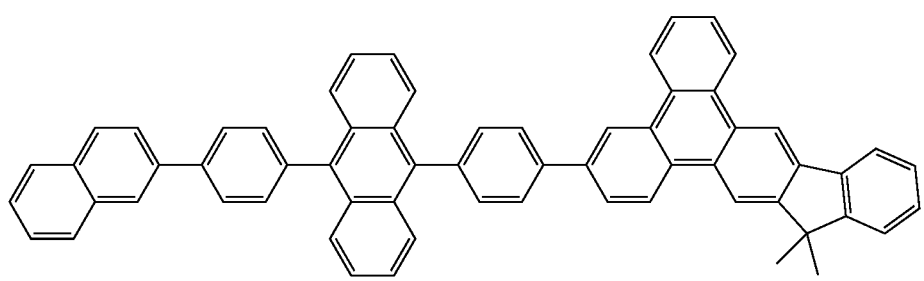
EX16
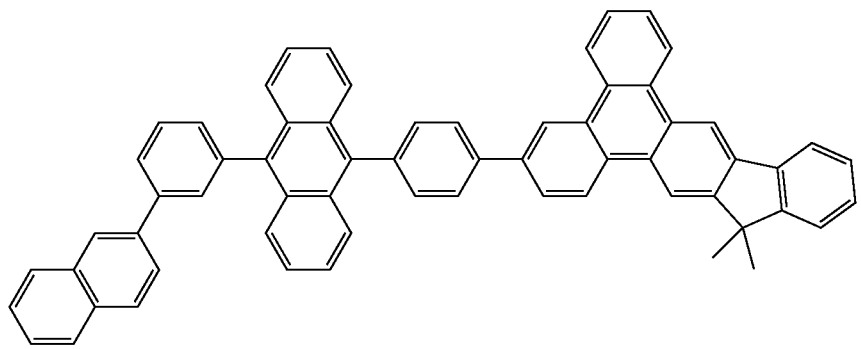
EX17
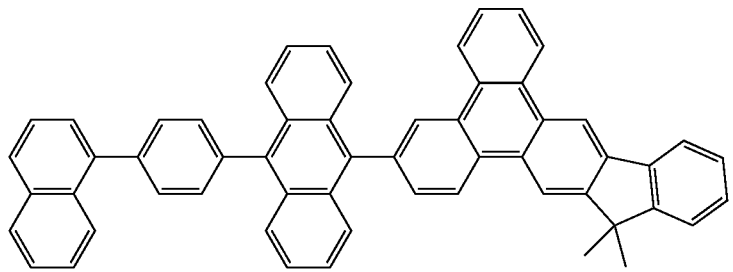

EX18
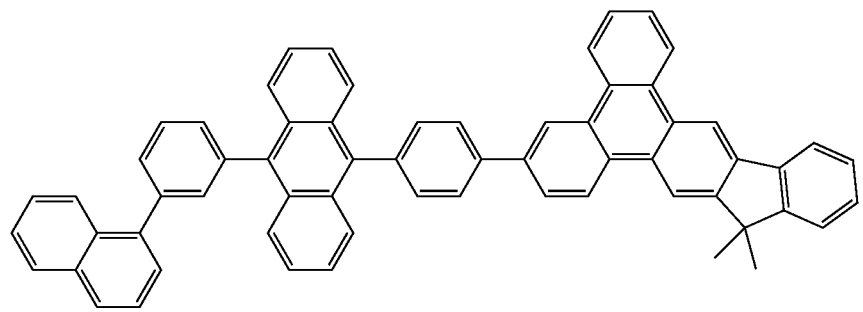
EX19
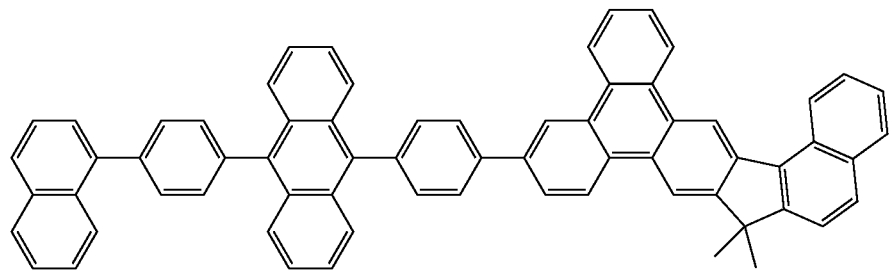
EX20
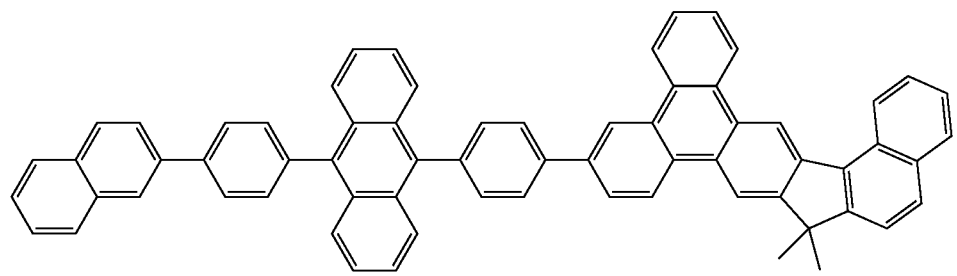
EX21
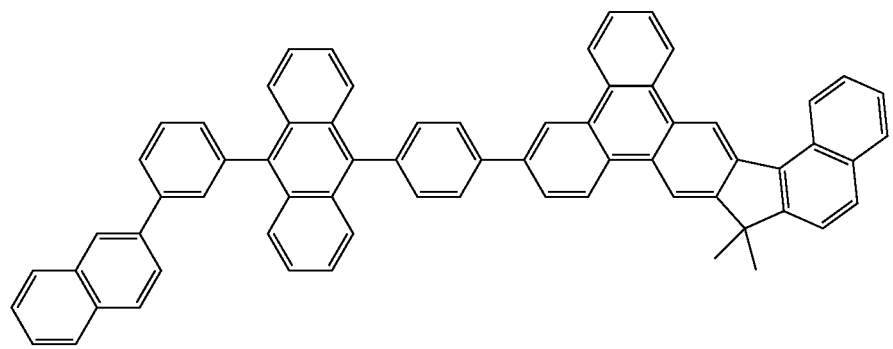
EX22
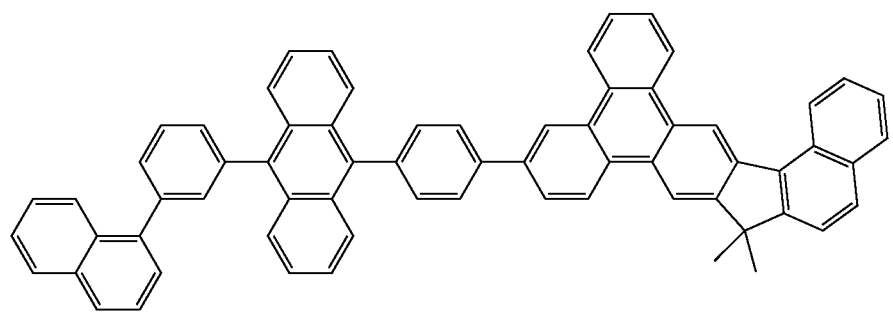

EX23
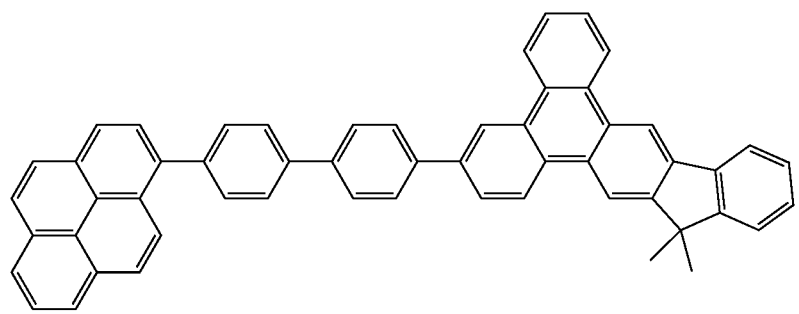
EX24
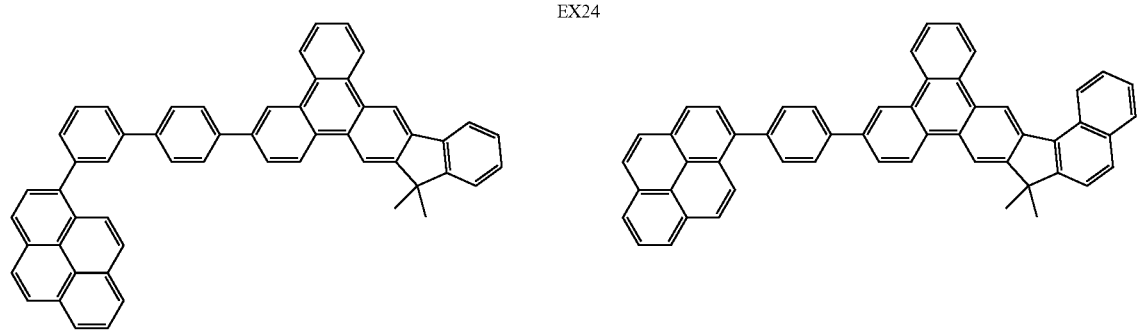
EX25
EX26
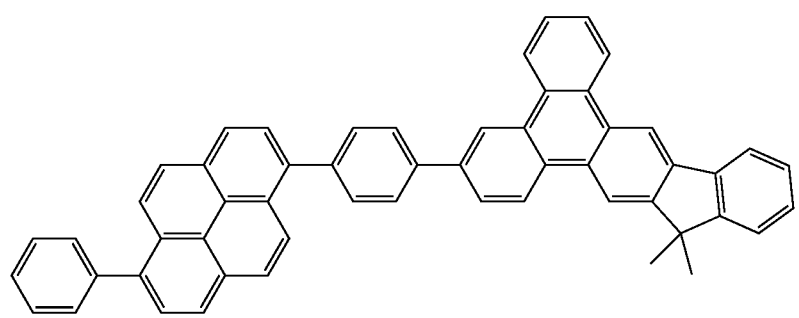
EX27
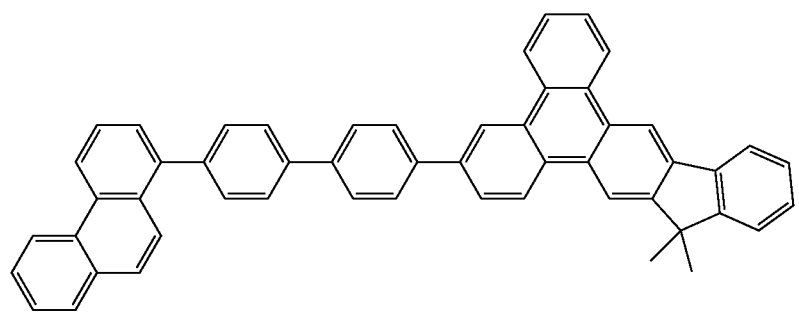
EX28
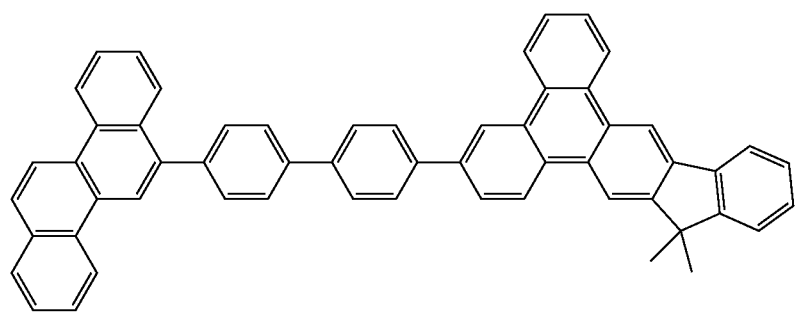

-continued
EX29
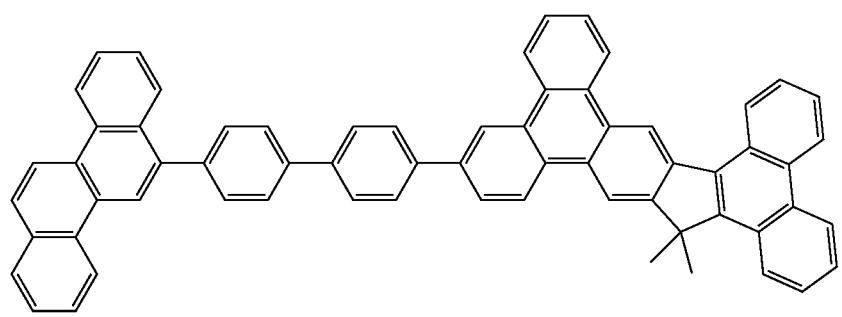
EX30
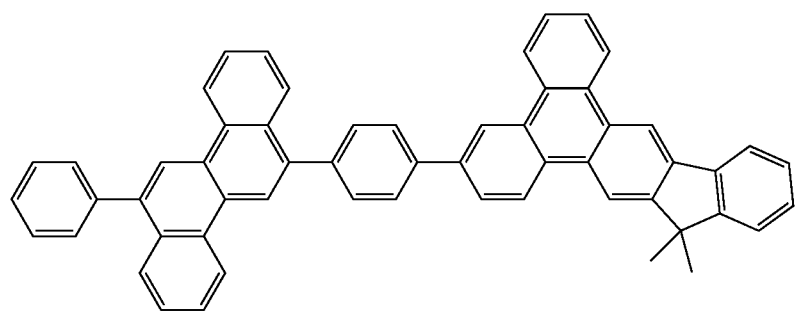
EX31
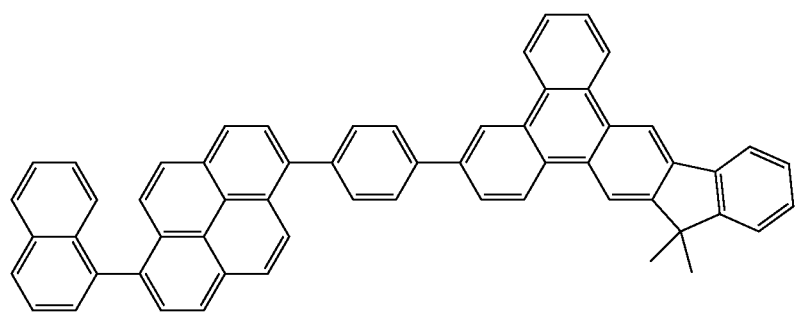
EX32
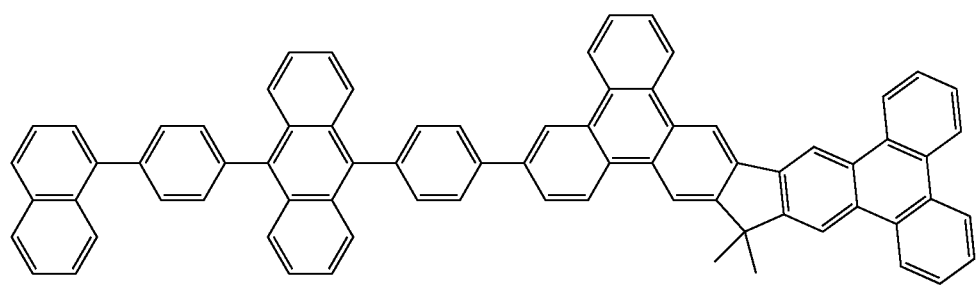
EX33
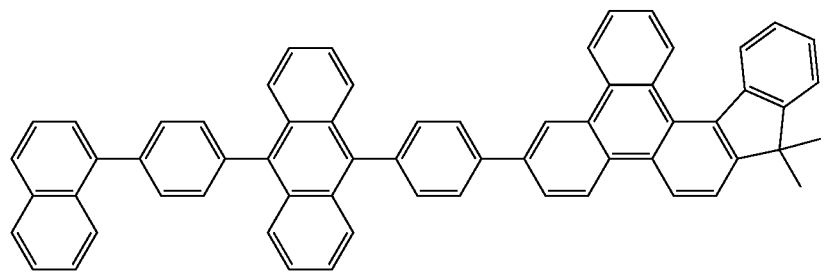

EX34

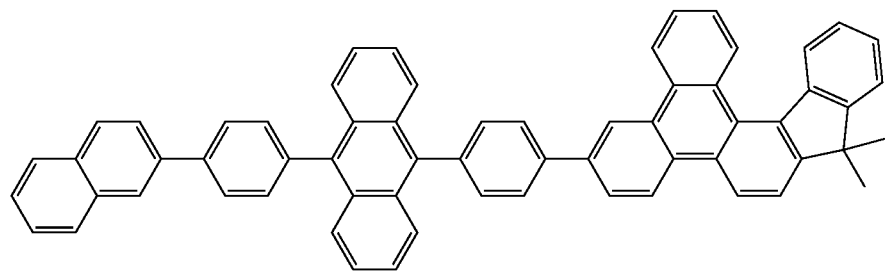

and

EX35

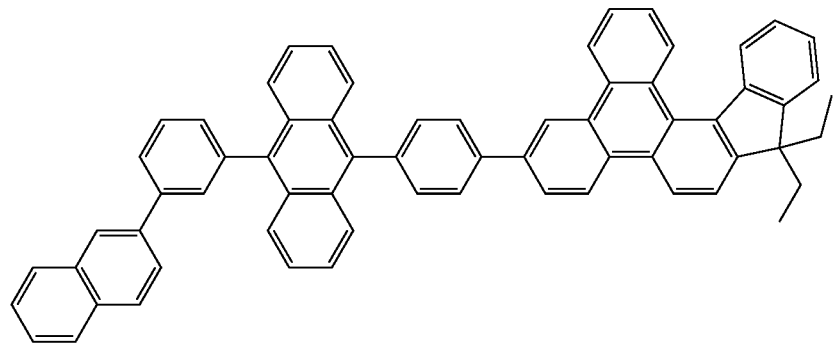

Detailed preparation for the compound in the present invention could be clarified by exemplary embodiments, but the present invention is not limited to exemplary embodiments. EXAMPLE 1~5 show the preparation for some EXAMPLES of the compound in the present invention. EXAMPLE 6~7 show the fabrication of organic EL device and I-V-B, life time of organic EL device testing report.

Example 1

Synthesis of EX7

Synthesis of 2-phenyl-4-nitrobromobenzene

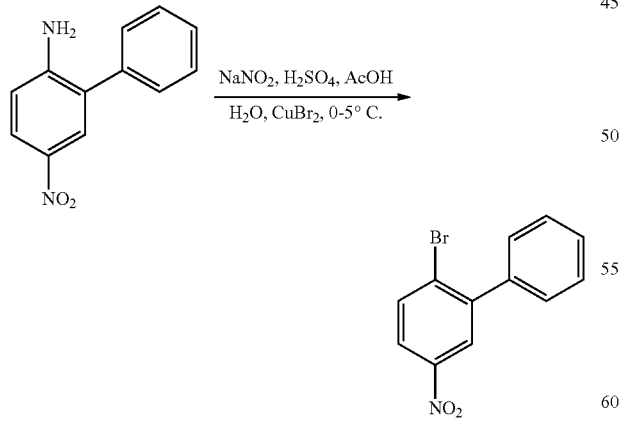

2.6 g (12.14 mmol) of 2-phenyl-4-nitroaniline was added to a mixture of 0.92 g (13.35 mmol) of sodium nitrite, 8 ml of sulfuric acid, 9 ml of acetic acid at 0-5° C. and stirred for 2 hours at 0-5° C. Water was added to this mixture and stirred for 1 hr at room temperature. 4.3 g (19.42 mmol) of copper(II) bromide dissolved in 9.3 ml 2M HCl solution was added and stirred for 20 min at room temperature, then heated to 60° C. for 1 hr. After finishing the reaction, the organic layer was extracted with ether and water, washed with brine, dried over magnesium sulfate and evaporated to dryness and the crude was purified by column chromatography on silica to give product (1.5 g, 5.39 mmol, 45.5%) as a white solid.

Synthesis of 2-(5-nitro-[1,1'-biphenyl]-2-yl)-9,9-dimethyl-9H-fluorene

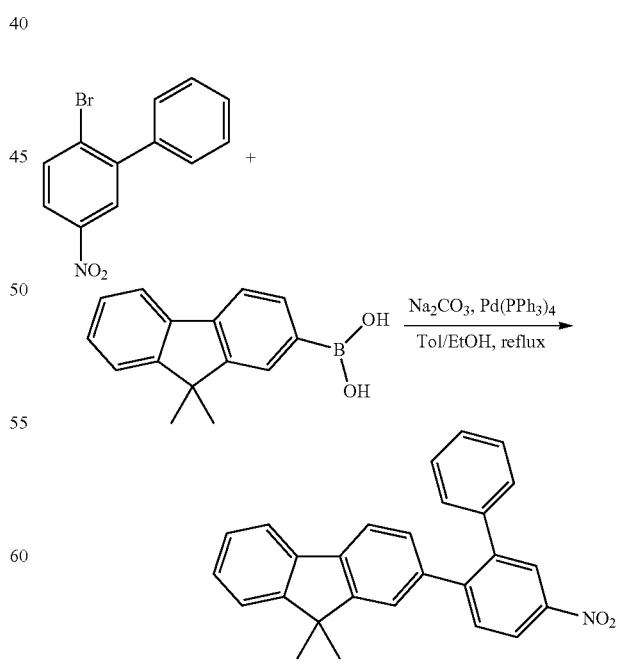

A mixture of 40 g (14.38 mmol) of 2-phenyl-4-nitrobromobenzene, 27.7 g (15.82 mmol) of 9,9-dimethyl-9H-fluoren-2-yl-2-boronic acid, 1.8 g (0.16 mmol) of Pd(PPh₃)₄, 119 ml of 2M Na₂CO₃, 150 ml of EtOH and 450 ml toluene was degassed and placed under nitrogen, and then heated at 90° C. overnight. After finishing the reaction, the mixture was allowed to cool to room temperature. The solution was extracted with dichloromethane and water. The organic layer was dried with anhydrous magnesium sulfate and the solvent was evaporated under reduced pressure. The residue was purified by column chromatography on silica (hexane-dichloromethane) to give product 43.1 g (110.1 mmol, 69.6%). 1H NMR (CDCl3, 400 MHz): chemical shift (ppm) 7.93 (s, 1H), 7.71 (d, 1H), 7.50 (d, 1H), 7.38-7.21 (m, 6H), 7.16~6.92 (m, 4H), 6.83~6.65 (m, 2H), 1.15 (s, 6H)

Synthesis of 2-(5-amino-[1,1'-bipheny]-2-yl)-9,9-dimethyl-9H-fluorene

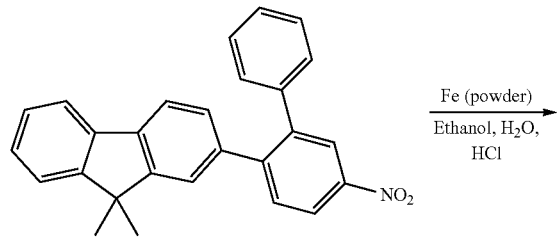

A mixture of 10.4 g (26.56 mmol) of 2-(5-nitro-[1,1'-biphenyl]-2-yl)-9,9-dimethyl-9H-fluorene, 8.5 g (159.36 mmol) of iron powder and 10 ml of conc. HCl was refluxed in aqueous ethanol (100 mL of alcohol and 30 mL of water) at 85° C. for 2 h. The reaction mixture was filtered and the filtrate was extracted with ethyl acetate and water. The organic layer was dried with anhydrous magnesium sulfate and the solvent was evaporated under reduced pressure. Formed solid was washed with hexane to yield product 8.2 g (22.68 mmol, 85%). 1H NMR (CDCl3, 400 MHz): chemical shift (ppm) 7.71 (d, 1H), 7.64 (d, 1H), 7.42 (d, 1H), 7.29~7.12 (m, 7H), 7.06 (d, 2H), 6.89 (s, 1H), 6.80 (d, 1H), 6.78 (s, 1H), 1.12 (s, 6H).

Synthesis of 2-(4-bromo-[1,1'-biphenyl]-2-yl)-9,9-dimethyl-9H-fluorene

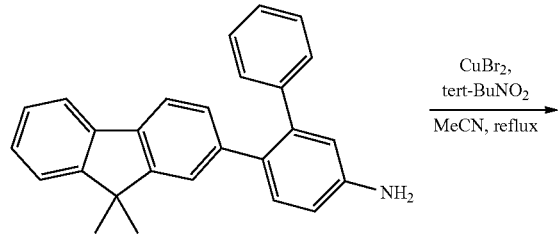

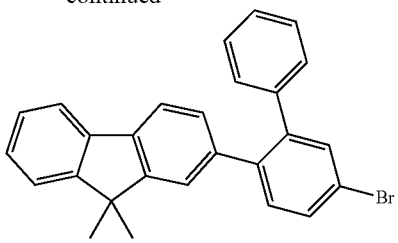

To a refluxing mixture of 0.34 g (3.32 mmol) of tert-butyl nitrite, 0.6 g (2.76 mmol) of anhydrous copper(II)bromide and anhydrous acetonitrile (46 mL), 1 g (2.76 mmol) of the corresponding 2-(4-amino-[1,1'-biphenyl]-2-yl) 9,9-dimethyl-9H-fluorene was added slowly over a period of 1 h giving rise to a reaction with vigorous foaming and evolution of nitrogen gas. After completion of the reaction, the mixture was cooled to room temperature and poured into an aqueous HCl solution. The crude which precipitated was purified by column chromatography on silica(hexane-dichloromethane) to give product 0.3 g (0.70 mmol, 25%). 1H NMR (CDCl3, 400 MHz): chemical shift (ppm) 7.81 (d, 1H), 7.40~7.65 (m, 1H), 7.66~7.68 (m, 1H), 7.61~7.63 (m, 1H), 7.35~7.37 (m, 1H), 7.24~7.32 (m, 4H), 7.15~7.22 (m, 4H), 7.09~7.12 (m, 2H), 6.93 (d, 1H), 1.20 (s, 6H).

Synthesis of 6-bromo-10,10-dimethyl-10H-indeno[2,1-b]triphenylene

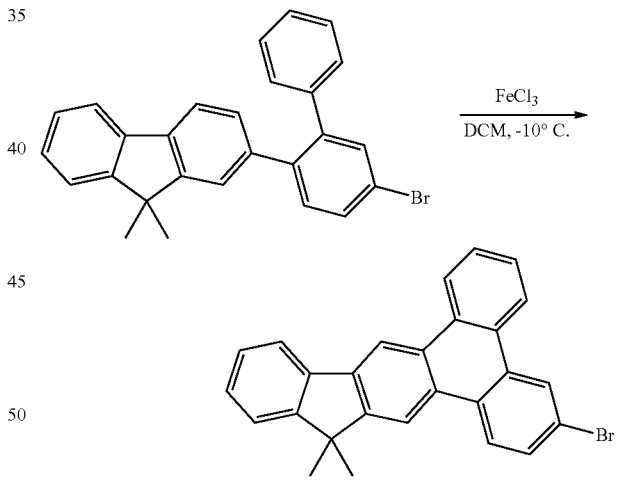

In a 100 ml three-necked flask that had been degassed and filled with nitrogen, 2.9 g (0.68 mmol) of 2-(4-bromo[1,1'-biphenyl]-2-yl)-9,9-dimethyl-9H-fluorene was dissolved in anhydrous dichloromethane (180 ml), 5.5 g (3.40 mmol) Iron(III)chloride was then added, and the mixture was stirred one hour. The reaction was quenched with methanol and water and the organic layer was separated and the solvent was removed. The residue was purified by column chromatography on silica(hexane-dichloromethane) afforded a white solid (1.7 g, 0.81 mmol, 58.6%). 1H NMR (CDCl3, 400 MHz): chemical shift (ppm) 9.01 (s, 1H), 8.94 (d, 2H), 8.78 (s, 1H), 8.58 (s, 1H), 8.49 (s, 1H), 7.98 (d, 1H), 7.78-7.85 (m, 2H), 7.43~7.63 (m, 4H), 1.69 (s, 6H).

Synthesis of 10,10-dimethyl-6-(10-(naphthalen-2-yl)anthracen-9-yl)-10H-indeno[2,1-b]triphenylene

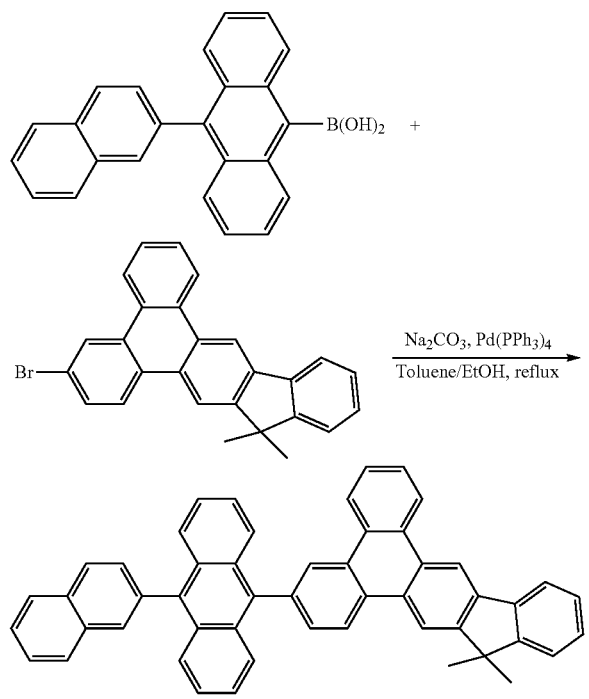

A mixture of 8.6 g (20.3 mmol) of 6-bromo-10,10-dimethyl-10H-indeno[2,1-b]triphenylene, 7.8 g (22.3 mmol) of 10-(naphthalen-2-yl)anthracen-9-ylboronic acid, 0.5 g (0.4 mmol) of Pd(PPh₃)₄, 21 ml of 2M Na₂CO₃, 17 ml of EtOH and 70 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (6.5 g, 10 mmol, 50%) as a yellow solid. 1H NMR (CDCl3, 400 MHz): chemical shift (ppm) 9.06 (s, 1H), 9.01 (d, 1H), 8.81~8.88 (m, 3H), 8.60 (d, 1H), 7.93~8.11 (m, 5H), 7.76~7.86 (m, 5H), 7.64~7.73 (m, 2H), 7.54~7.63 (m, 4H), 7.40~7.48 (m, 2H), 7.34~7.31 (m, 4H), 1.71 (s, 6H).

Example 2

Synthesis of EX9

Synthesis of 110,10-dimethyl-6-(4-(10-(naphthalen-2-yl) anthracen-9-yl)phenyl)-10H-indeno[2,1-b]triphenylene

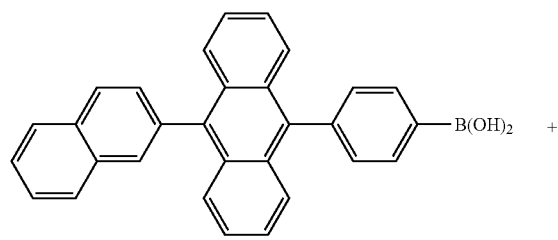

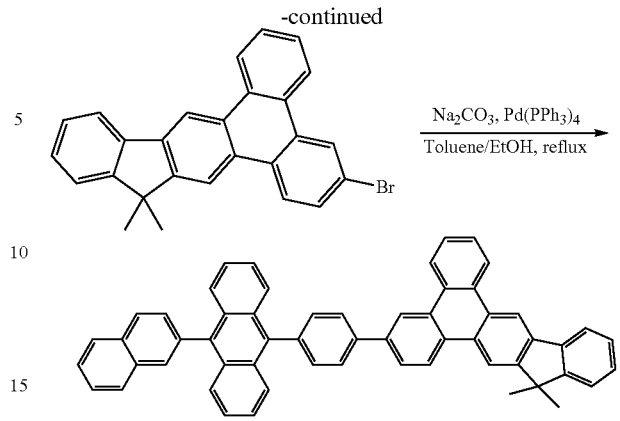

A mixture of 8.6 g (20.3 mmol) of 6-bromo-10,10-dimethyl-10H-indeno[2,1-b]triphenylene, 9.5 g (22.3 mmol) of 4-(10-(naphthalen-2-yl) anthracen-9-yl)phenylboronic acid, 0.5 g (0.4 mmol) of Pd(PPh₃)₄, 21 ml of 2M Na₂CO₃, 17 ml of EtOH and 70 ml Toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (7.3 g, 10 mmol, 50%) as a yellow solid. 1H NMR (CDCl3, 400 MHz): chemical shift (ppm) 9.06 (s, 1H), 9.01 (d, 1H), 8.81~8.88 (m, 3H), 8.60 (d, 1H), 7.93~8.11 (m, 5H), 7.76~7.86 (m, 5H), 7.64-7.73 (m, 2H), 7.54~7.63 (m, 4H), 7.40~7.48 (m, 2H), 7.34~7.25 (m, 8H), 1.71 (s, 6H).

Example 3

Synthesis of EX17

Synthesis of 2-(10,10-dimethyl-10H-indeno[2,1-b]triphenylen-12-yl)quinoline

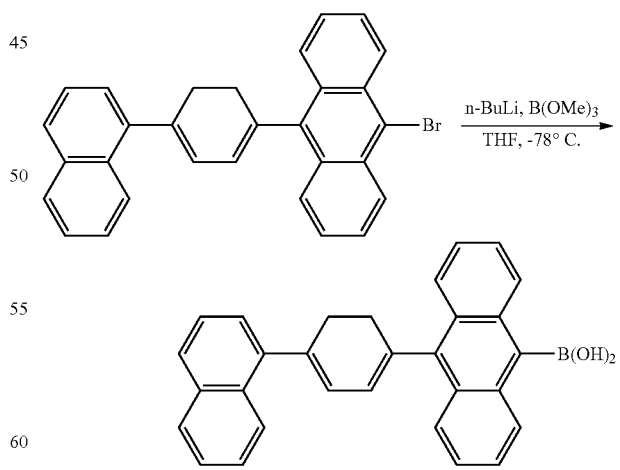

In a 500 ml three-necked flask that had been degassed and filled with nitrogen, 10 g (21.7 mmol) of 9-bromo-10-(4-(naphthalen-1-yl) cyclohexa-1,3-dienyl)anthracene was dissolved in anhydrous THF (150 ml) cool to −78° C., 10.4 ml (26.1 mmol) of n-butyllithium (2.5M) was then added and stir 1 hour, 3.4 g (32.6 mmol) of trimethyl borate was then added and hexane-dichloromethane stir overnight, After finishing the reaction, the solution was extracted with 300 ml of ethyl acetate and 200 ml of water. The organic layer was dried with anhydrous magnesium sulfate and the solvent was evaporated under reduced pressure to give product 7.4 g (80%) as a yellow solid.

Synthesis of 10,10-dimethyl-6-(10-(4-(naphthalen-1-yl)phenyl) anthracen-9-yl)-10H-indeno[2,1-b]triphenylene

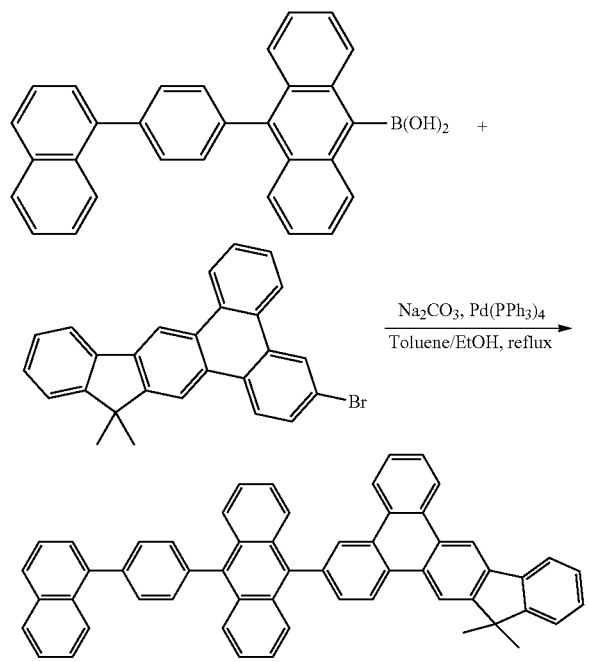

A mixture of 8.6 g (20.3 mmol) of 6-bromo-10,10-dimethyl-10H-indeno[2,1-b]triphenylene, 9.5 g (22.3 mmol) of 10-(4-(naphthalen-1-yl) cyclohexa-1,3-dienyl)anthracen-9-ylboronic acid, 0.5 g (0.4 mmol) of Pd(PPh$_3$)$_4$, 21 ml of 2M Na$_2$CO$_3$, 17 ml of EtOH and 70 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (5.9 g, 8.1 mmol, 40%) as a yellow solid. 1H NMR (CDCl3, 400 MHz): chemical shift (ppm) 9.06 (s, 1H), 9.02 (d, 1H), 8.83~8.88 (m, 3H), 8.61 (d, 1H), 8.19~8.21 (m, 1H), 8.03~7.92 (m, 5H), 7.87-7.84 (m, 3H), 7.78~7.70 (m, 3H), 7.70~7.54 (m, 8H), 7.48~7.35 (m, 6H), 1.71 (s, 6H).

Example 4

Synthesis of EX26

Synthesis of 4,4,5,5-tetramethyl-2-(6-phenylpyren-1-yl)-1,3,2-dioxaborolane

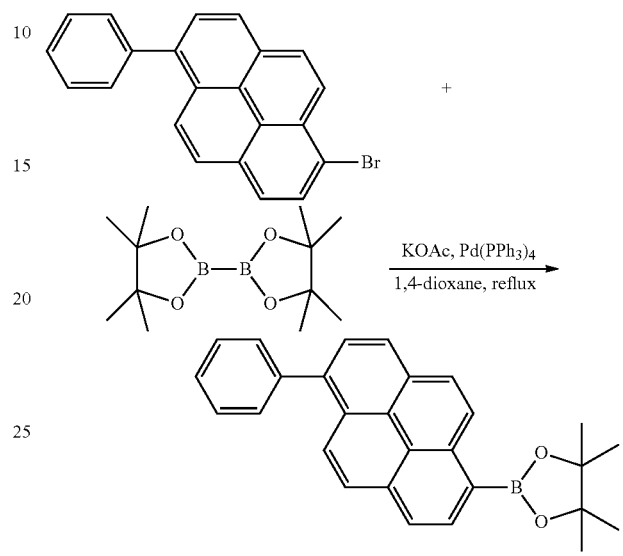

A mixture of 13.1 g (37 mmol) of 1-bromo-6-phenylpyrene, 11.25 g (44.3 mmol) of bis(pinacolato)diboron, 0.44 g (0.38 mmol) of Pd(PPh$_3$)$_4$, 10.8 g (110 mmol) of potassium acetate, and 440 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (10.5 g, 26 mmol, 70%) as a light-yellow solid.

Synthesis of 1-(4-bromophenyl)-6-phenylpyrene

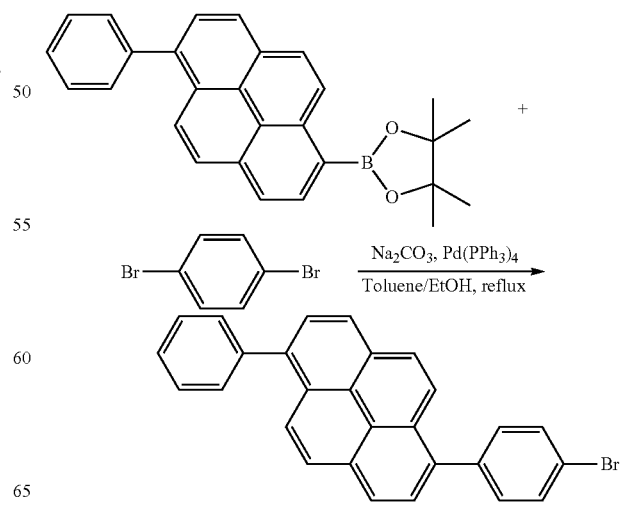

A mixture of 10.5 g (26 mmol) of 4,4,5,5-tetramethyl-2-(6-phenyl pyren-1-yl)-1,3,2-dioxaborolane, 12 g (52 mmol) of 1,4-dibromobenzene, 0.58 g (0.5 mmol) of Pd(PPh₃)₄, 39 ml of 2M Na₂CO₃, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica to give product (5.6 g, 13 mmol, 50%) as a light-yellow solid.

Synthesis of 4,4,5,5-tetramethyl-2-(4-(6-phenylpyren-1-yl) phenyl)-1,3,2-dioxaborolane

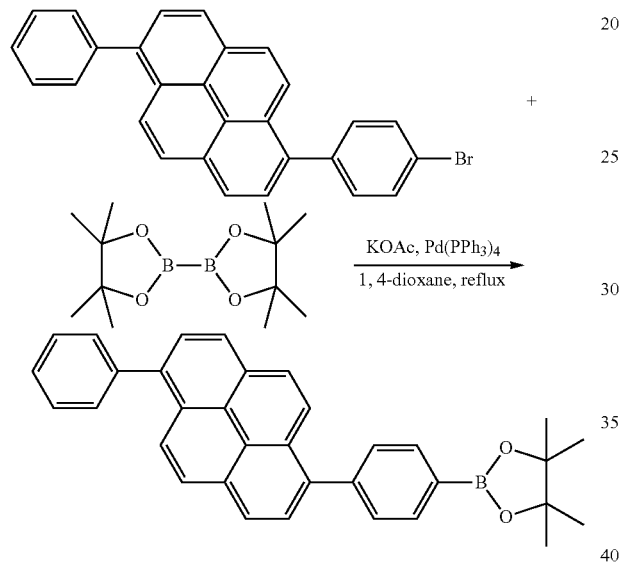

A mixture of 5.6 g (13 mmol) of 1-(4-bromophenyl)-6-phenyl pyrene, 4.9 g (19.5 mmol) of bis(pinacolato)diboron, 0.15 g (0.13 mmol) of Pd(PPh₃)₄, 3.8 g (39 mmol) of potassium acetate, and 180 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (4.36 g, 9.1 mmol, 70%) as a light-yellow solid.

Synthesis of 10,10-dimethyl-6-(4-(6-phenylpyren-1-yl)phenyl)-10H-indeno[2,1-b]triphenylene

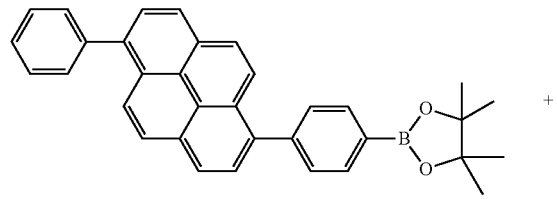

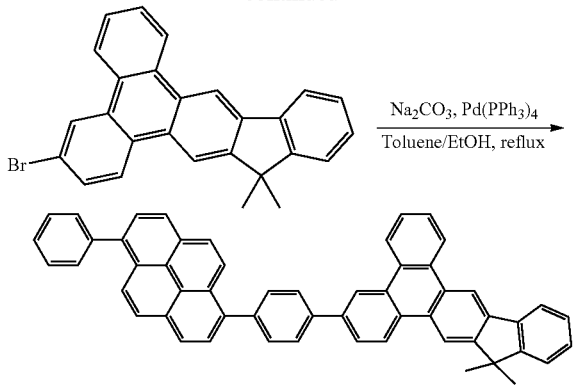

A mixture of 4.36 g (9.1 mmol) of 4,4,5,5-tetramethyl-2-(4-(6-phenylpyren-1-yl)phenyl)-1,3,2-dioxaborolane, 3.8 g (9.1 mmol) of 6-bromo-10,10-dimethyl-10H-indeno[2,1-b]triphenylene, 0.1 g (0.09 mmol) of Pd(PPh₃)₄, 14 ml of 2M Na₂CO₃, 28 ml of EtOH and 56 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica(hexane-dichloromethane) to give product (4.43 g, 6.37 mmol, 70%) as a light-yellow solid; 1H NMR (CDCl3, 400 MHz): chemical shift (ppm) 9.01 (s, 1H), 8.85~8.73 (m, 4H), 8.33~8.19 (m, 4H), 8.07~7.96 (m, 8H), 7.64-7.83 (m, 6H), 7.57~7.41 (m, 6H), 1.69 (s, 6H).

Example 5

Synthesis of EX31

Synthesis of 4,4,5,5-tetramethyl-2-(6-(naphthalen-1-yl) pyren-1-yl)-1,3,2-dioxaborolane

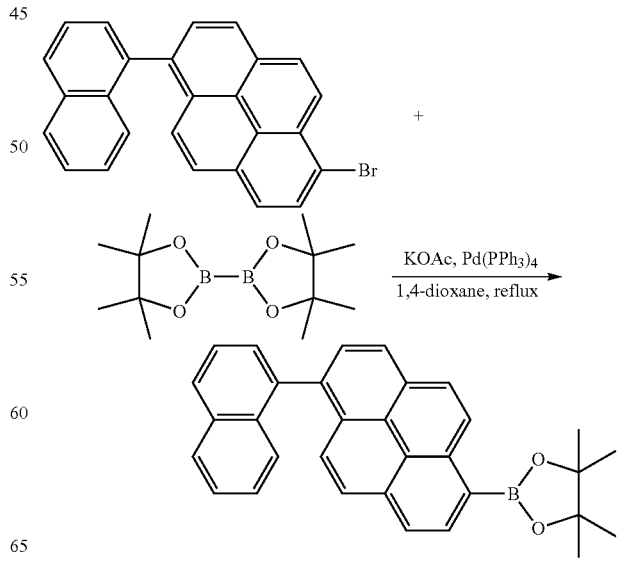

A mixture of 15 g (37 mmol) of 1-bromo-6-(naphthalen-1-yl)pyrene, 11.25 g (44.3 mmol) of bis(pinacolato)diboron, 0.44 g (0.38 mmol) of Pd(PPh$_3$)$_4$, 10.8 g (110 mmol) of potassium acetate, and 440 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (11.8 g, 26 mmol, 70%) as a light-yellow solid.

Synthesis of 1-(4-bromophenyl)-6-(naphthalen-1-yl)pyrene

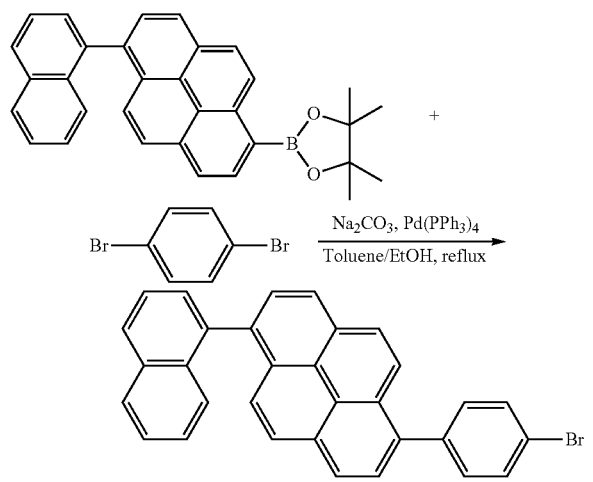

A mixture of 11.8 g (26 mmol) of 4,4,5,5-tetramethyl-2-(6-(naphthalen-1-yl)pyren-1-yl)-1,3,2-dioxaborolane, 12 g (52 mmol) of 1,4-dibromobenzene, 0.58 g (0.5 mmol) of Pd(PPh$_3$)$_4$, 39 ml of 2M Na$_2$CO$_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica to give product (6.3 g, 13 mmol, 50%) as a light-yellow solid.

Synthesis of 4,4,5,5-tetramethyl-2-(4-(6-(naphthalen-1-yl) pyren-1-yl)phenyl)-1,3,2-dioxaborolane

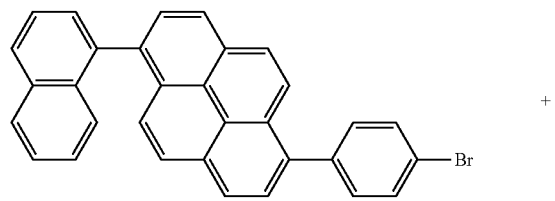

-continued

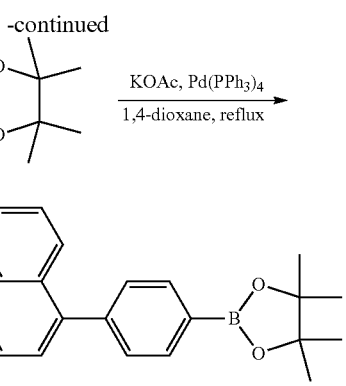

A mixture of 6.3 g (15 mmol) of 1-(4-bromophenyl)-6-(naphthalene-1-yl)pyrene, 5.7 g (22.5 mmol) of bis(pinacolato)diboron, 0.17 g (0.15 mmol) of Pd(PPh$_3$)$_4$, 4.4 g (45 mmol) of potassium acetate, and 180 ml 1,4-dioxane was degassed and placed under nitrogen, and then heated at 90° C. for 14 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (6.4 g, 12 mmol, 80%) as a light-yellow solid.

Synthesis of 10,10-dimethyl-6-(4-(6-(naphthalen-1-yl)pyren-1-yl)phenyl)-10H-indeno[2,1-b]triphenylene

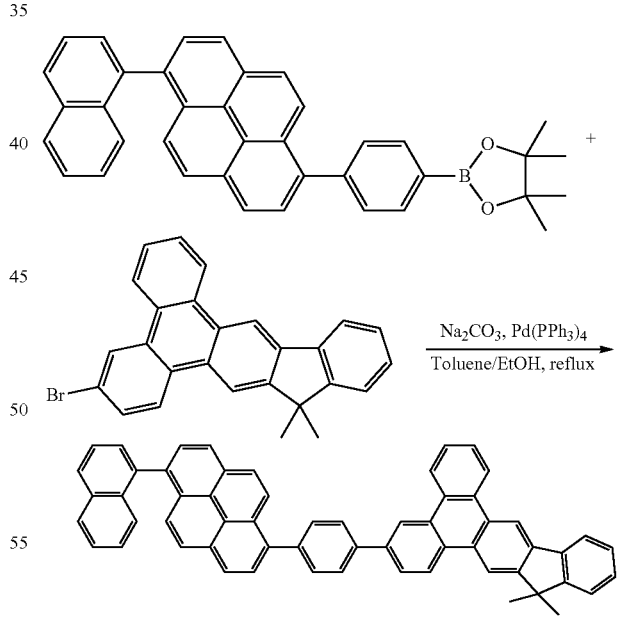

A mixture of 6.4 g (12 mmol) of 4,4,5,5-tetramethyl-2-(4-(6-(naphthalen-1-yl)pyren-1-yl)phenyl)-1,3,2-dioxaborolane, 5 g (12 mmol) of 6-bromo-10,10-dimethyl-10H-indeno[2,1-b]triphenylene, 0.14 g (0.12 mmol) of Pd(PPh$_3$)$_4$, 18 ml of 2M Na$_2$CO$_3$, 20 ml of EtOH and 40 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica(hexane-dichloromethane) to give product (6.26 g, 8.4 mmol, 70%) as a light-yellow solid; 1H NMR (CDCl3, 400 MHz): chemical shift (ppm) 9.01 (d, 1H), 9.00 (s, 1H), 8.88~8.81 (m, 3H), 8.74 (s, 1H), 8.7 (d, 1H), 8.28 (d, 1H), 8.22 (d, 1H), 8.15 (d, 1H), 8.08~7.99 (m, 8H), 7.92 (d, 1H), 7.83 (d, 1H), 7.75~7.63 (m, 5H), 7.55~7.39 (m, 5H), 7.30~7.27 (m, 1H), 1.69 (s, 6H)

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f: 2,3-]quinoxaline-2,3,6,7,10,11-hexacarbonitrile (HAT-CN) is used as hole injection layer in this organic EL device. N,N-Bis(naphthalene-1-yl)-N,N-bis (phenyl)-benzidine (NPB) is most widely used as the hole transporting layer. 10,10-Dimethyl-12-(4-(pyren-1-yl)phenyl)-10H-indeno[1,2-b]triphenylene(PT-312, US20140175384) or 10,10-dimethyl-12-(10-(naphthalen-2-yl)anthracen-9-yl)-10H-indeno[2,1-b]triphenylene (PT-3 13, US20140209866) is used as blue emitting host in organic EL device for comparison and N1,N1,N6,N6-tetramtolylpyrene-1,6-diamine (D1) is used as blue guest. 2-(10, 10-dimethyl-10H-indeno[2,1-b]triphenylen-13-yl)-9-phenyl-1,10-phenanthroline is used as electron transporting material (ET1) to co-deposit with 5% Li, 2-(10,10-dimethyl-10H-indeno[2,1-b]triphenylen-12-yl)-4,6-diphenyl-1,3,5-triazine (ET2), 2-(10,10-dimethyl-10H-indeno[2,1-b] triphenylen-13-yl)-4,6-bis 5-phenylbiphenyl-3-yl)-1,3,5-triazineto (ET3) or 2,9-di(naphthalen-2-yl)-4,7-diphenyl-1, 10-phenanthroline (ET4) is used as electron transporting material to co-deposit with 8-hydroxyquinolato-lithium (LiQ) in organic EL device for comparison. Tris(2-phenylpyridinato)iridium(III) (D2) is used as phosphorescent dopant. 4-(10,10-dimethyl-10H-indeno[2,1-b] triphenylen-13-yl)dibenzo[b,d]thiophene (H1) is used as hole blocking material or emitting host in organic phosphorescent EL device. The prior art of OLED materials for producing standard organic EL device control and comparable material in this invention shown its chemical structure as follows:

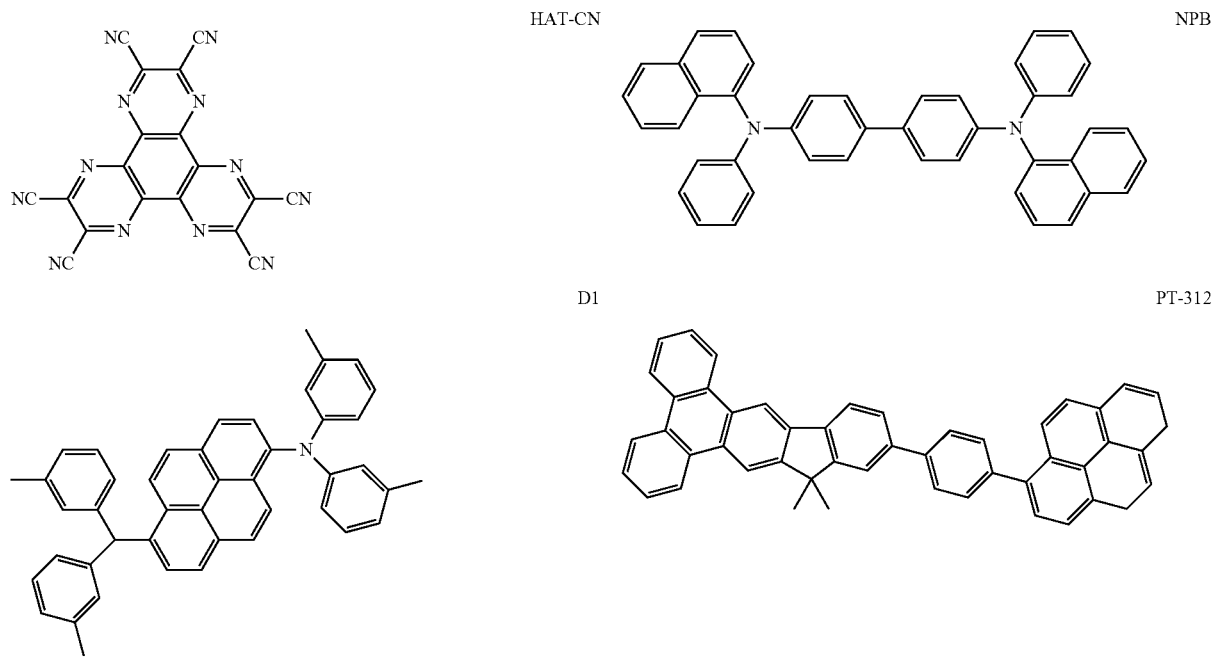

HAT-CN

NPB

D1

PT-312

-continued
PT-313
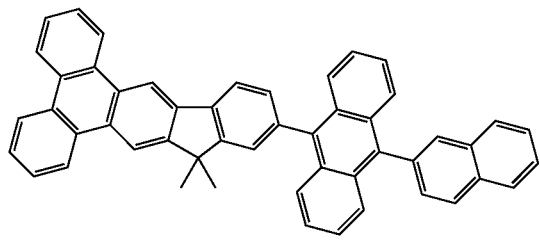
LiQ
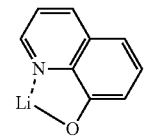
ET1
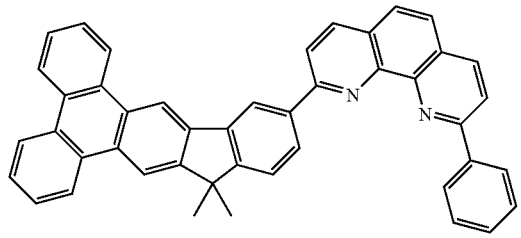
ET2
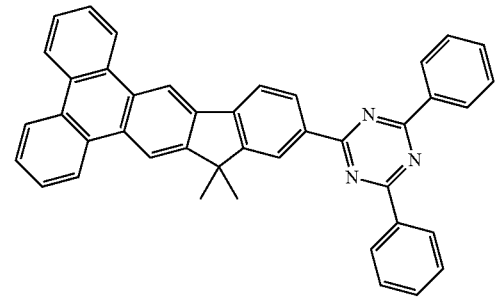
ET3
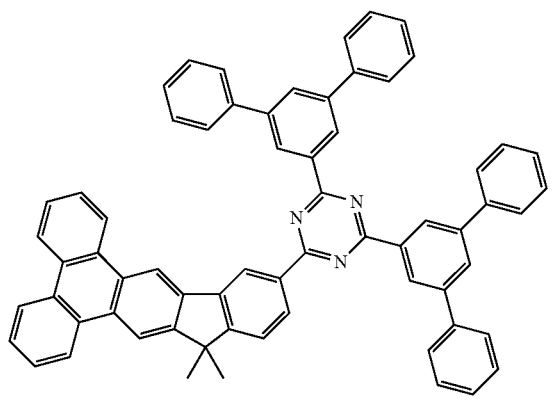
ET4
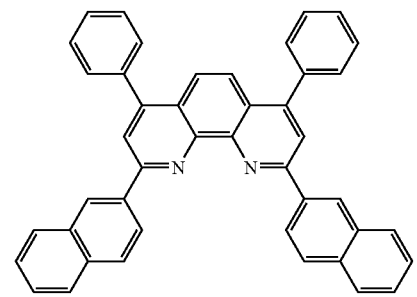
H1
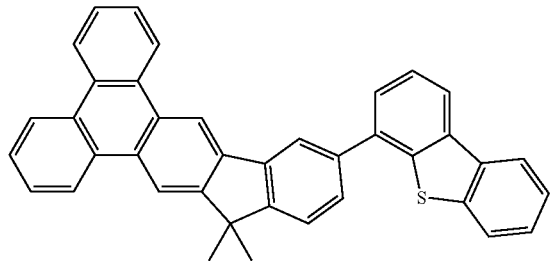
D2
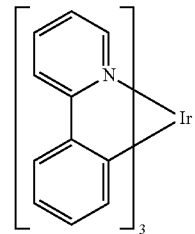
EX1
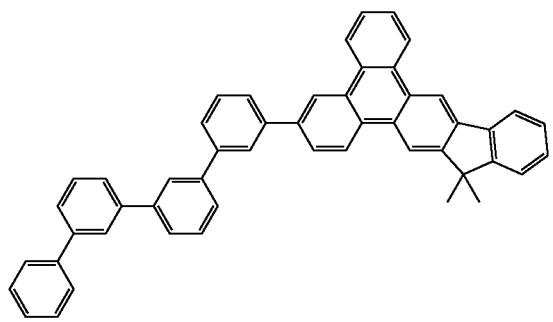
EX7
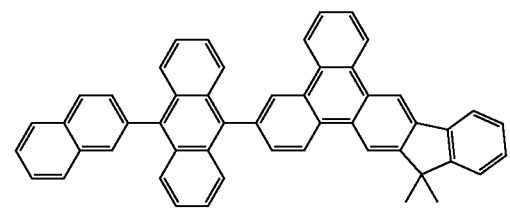

-continued

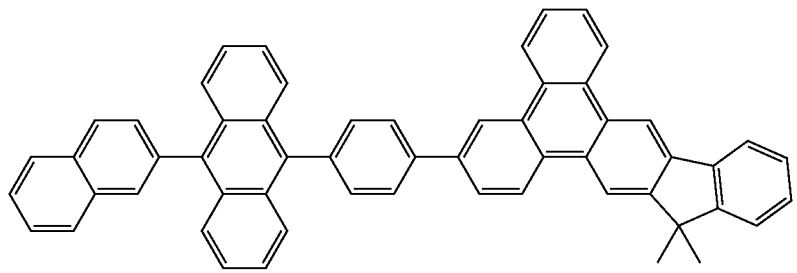

EX9

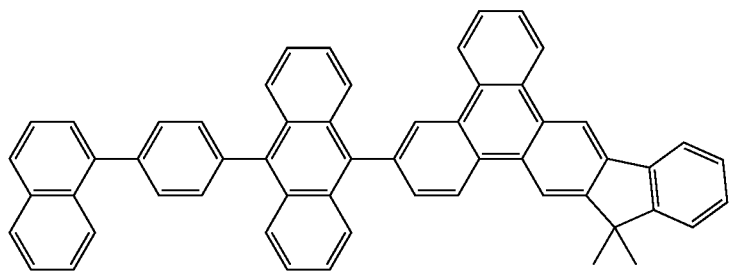

EX17

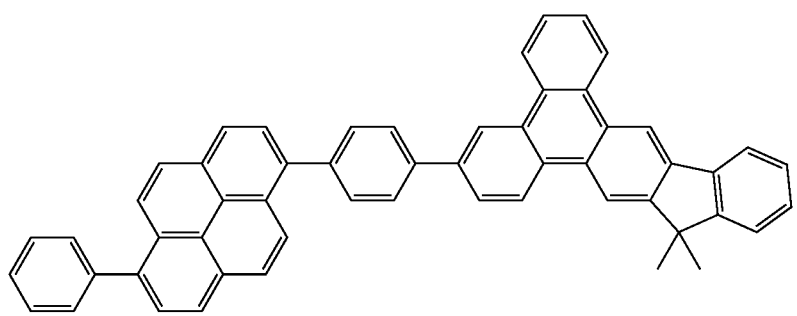

EX26

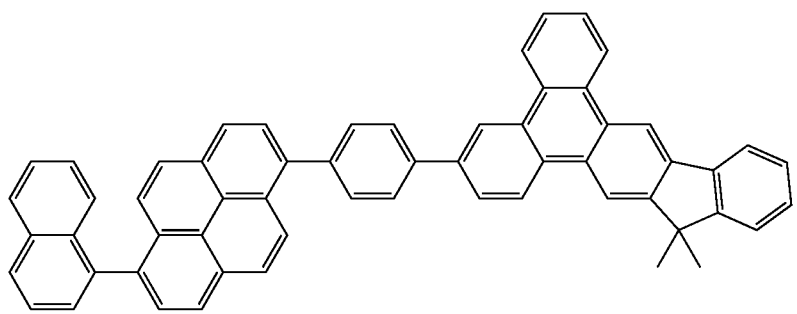

EX31

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 6

Using a procedure analogous to the above mentioned general method, fluorescent blue-emitting organic EL device having the following device structure I and II was produced (See FIG. 1). Device I: ITO/HAT-CN (20 nm)/NPB (130 nm)/fluorescent host doped 5% D1 (30 nm)/ET2 (10 nm)/ETM doped 5% Li (35 nm)/Al (160 nm). Device II: ITO/HAT-CN (20 nm)/NPB (130 nm)/fluorescent host doped 5% D1 (30 nm)/ET2 (10 nm)/ETM co-deposit 50% LiQ (35 nm)/LiQ (1 nm)/Al (160 nm). The I-V-B (at 1000 nits) and half-life time of fluorescent blue-emitting organic EL device testing report as Table 1 and Table 2, The half-life time is defined that the initial luminance of 1000 cd/m² has dropped to half.

TABLE 1

| Fluorescent Host | ETM doped 5% Li | Voltage (V) | Efficiency (cd/A) | CIE (y) | Half-life time (hour) |
|---|---|---|---|---|---|
| PT-312 | ET1 | 4.5 | 4.3 | 0.182 | 450 |
| PT-313 | ET1 | 4.5 | 4.1 | 0.185 | 480 |
| EX7 | ET1 | 4.3 | 5.2 | 0.182 | 350 |
| EX9 | ET1 | 4.8 | 5.6 | 0.191 | 580 |
| EX17 | ET1 | 4.5 | 5.3 | 0.193 | 480 |
| EX26 | ET1 | 4.8 | 5.0 | 0.182 | 450 |
| EX31 | ET1 | 4.6 | 5.5 | 0.182 | 480 |
| EX9 | ET4 | 6.5 | 4.5 | 0.188 | 250 |

TABLE 2

| Fluorescent Host | ETM co-deposit 50% LiQ | Voltage (V) | Efficiency (cd/A) | CIE (y) | Half-life time (hour) |
|---|---|---|---|---|---|
| PT-312 | ET3 | 6.5 | 4.3 | 0.181 | 460 |
| PT-313 | ET3 | 6.0 | 4.8 | 0.180 | 460 |
| EX7 | ET3 | 5.8 | 5.0 | 0.178 | 580 |
| EX9 | ET3 | 5.6 | 6.0 | 0.179 | 550 |
| EX17 | ET3 | 5.5 | 5.7 | 0.179 | 580 |
| EX26 | ET3 | 5.5 | 5.5 | 0.177 | 520 |
| EX31 | ET3 | 5.3 | 5.6 | 0.178 | 400 |
| EX9 | ET2 | 5.6 | 5.5 | 0.179 | 520 |
| EX17 | ET2 | 5.5 | 5.4 | 0.178 | 570 |
| EX9 | ET4 | 7.0 | 3.5 | 0.183 | 310 |

Example 7

Using a procedure analogous to the above mentioned general method, phosphorescent emitting organic EL device having the following device structures are produced (See FIG. 1.): ITO/HAT-CN (20 nm)/NPB (130 nm)/phosphorescent host (PHhost)+12% D2 (30 nm)/H1 (15 nm)/ET2 co-deposit 50% LiQ (40 nm)/LiQ (1 nm)/Al (160 nm). The I-V-B (at 1000 nits) and half-life time of phosphorescent emitting organic EL device testing report as Table 3. The half-life time is defined that the initial luminance of 3000 cd/m² has dropped to half.

TABLE 3

| PHhost | HBM | ETM | Voltage (V) | Efficiency (cd/A) | CIE (x, y) | Half-life time (hour) |
|---|---|---|---|---|---|---|
| EX1 | H1 | ET3 | 4.8 | 30 | 0.36, 0.55 | 550 |
| EX7 | H1 | ET3 | 4.5 | 17 | 0.36, 0.55 | 260 |
| EX1 | H1 | ET2 | 4.5 | 32 | 0.36, 0.55 | 650 |
| EX7 | H1 | ET2 | 4.6 | 16 | 0.35, 0.56 | 220 |
| EX1 | ET2 | ET3 | 3.8 | 38 | 0.36, 0.57 | 800 |
| H1 | ET2 | ET3 | 4.2 | 28 | 0.37, 0.57 | 600 |

In the above preferred embodiments for organic EL device test report (see Table 1 to Table 3), we show that with a general formula(I) in the present invention display good performance for fluorescent host and more purposes (EX1 is used for phosphorescent host) than the prior art of OLED materials US20140131664A1, US20140175384A1 and US20140209866A1. More specifically, the organic EL device in the present invention to collocate with H1 (hole blocking layer or phosphorescent host) and ET1, ET2 or ET3 (electron transporting layer) shown lower power consumption, higher efficiency and longer half-life time than the prior art of OLED materials ET4.

To sum up, the present invention discloses a compound which can be used for organic EL device is disclosed. More specifically, an organic EL device employing the compound as fluorescent emitting host, phosphorescent emitting host. The mentioned compound are represented by the following formula(I)

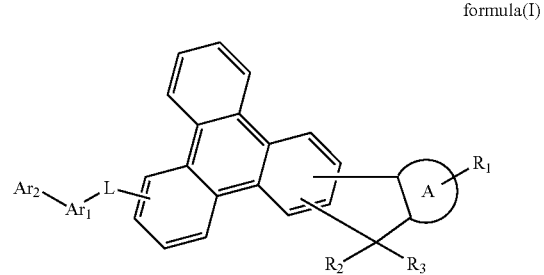

formula(I)

wherein A represents a phenyl group and a substituted or unsubstituted fused ring hydrocarbon units with two to four rings group, L represents a single bond or a substituted or unsubstituted divalent arylene group having 6 to 30 ring carbon atoms, $Ar_1$ and $Ar_2$ independently are selected from the group consisting of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group and a substituted or unsubstituted chrysenyl group; $R_1$ to $R_3$ independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A compound with a general formula(I) as follows:

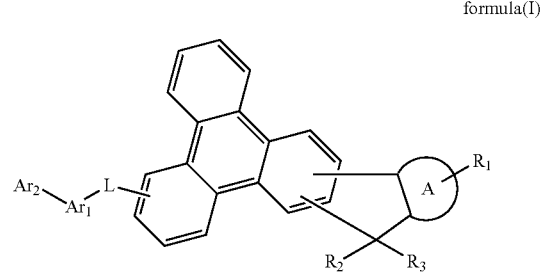

formula(I)

wherein A represents a phenyl group or a substituted or unsubstituted fused ring hydrocarbon unit with two to four rings, L represents a substituted or unsubstituted divalent arylene group having 6 to 30 ring carbon atoms, $Ar_1$ and $Ar_2$ independently are selected from the group consisting of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group and a substituted or unsubstituted chrysenyl group; $R_1$ to $R_3$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

2. The compound according to claim 1, wherein L is represented the following formulas:

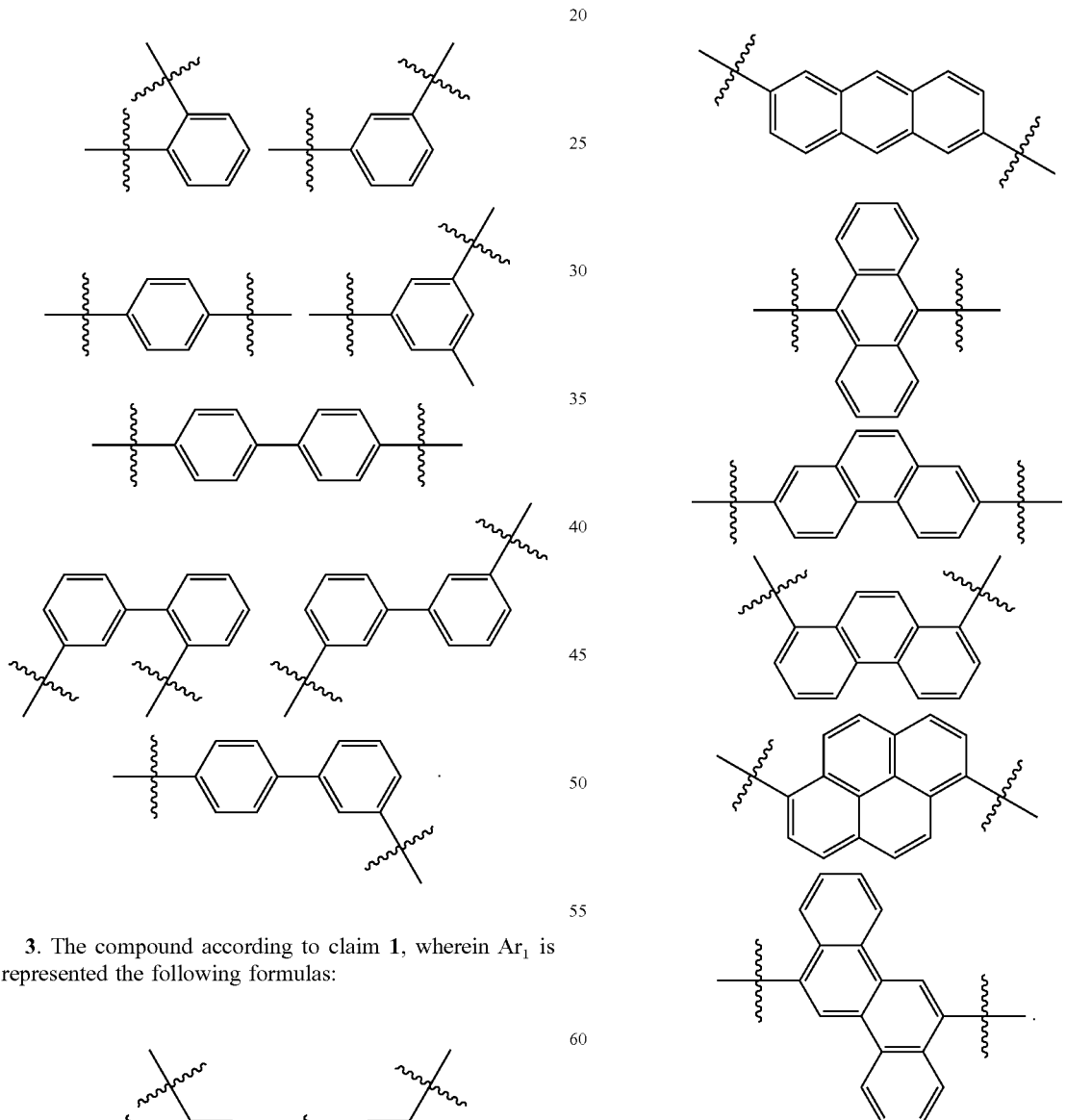

3. The compound according to claim 1, wherein $Ar_1$ is represented the following formulas:

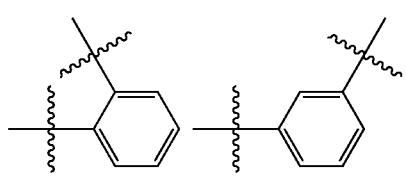

4. The compound according to claim 1, wherein $Ar_2$ is represented the following formulas:

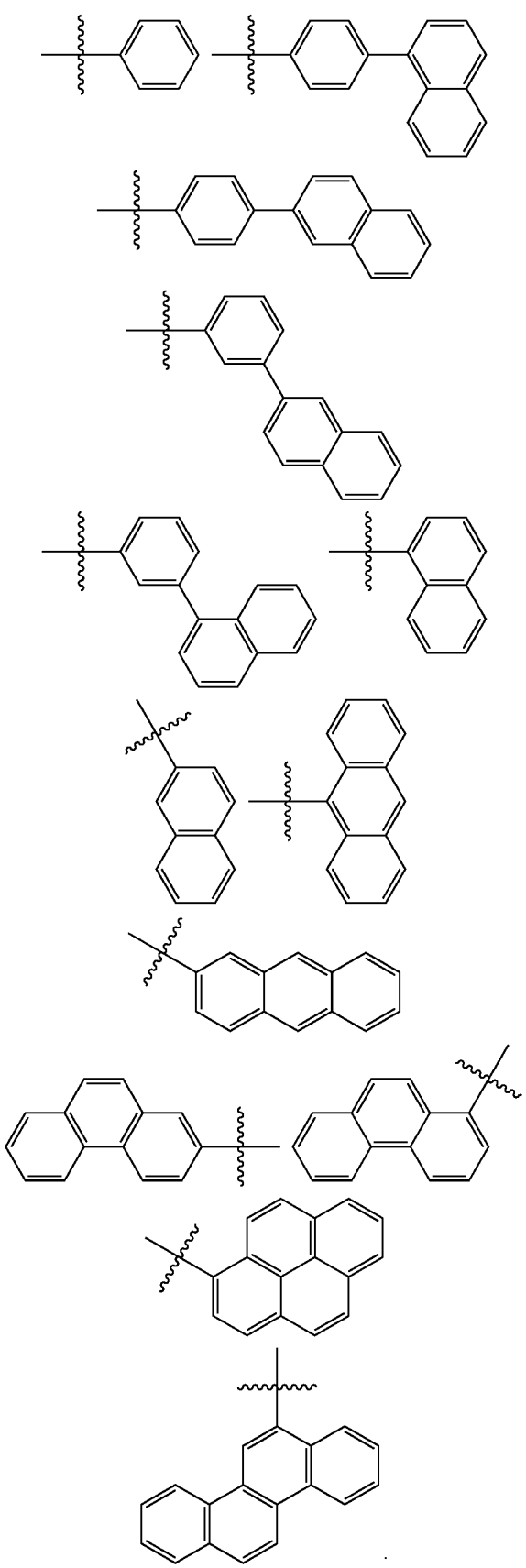

5. A compound of formula(III):

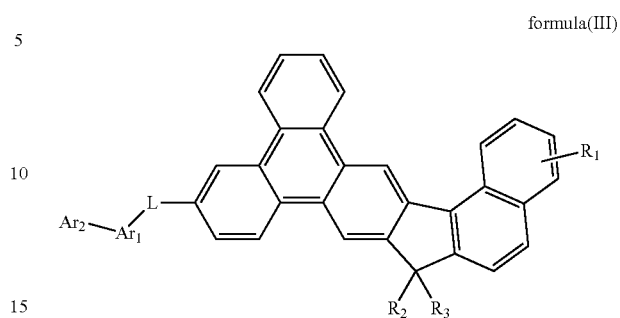

wherein L represents a single bond or a substituted or unsubstituted divalent arylene group having 6 to 30 ring carbon atoms, $Ar_1$ and $Ar_2$ independently are selected from the group consisting of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group and a substituted or unsubstituted chrysenyl group; $R_1$ to $R_3$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

6. The compound according to claim 5, wherein L is represented the following formulas:

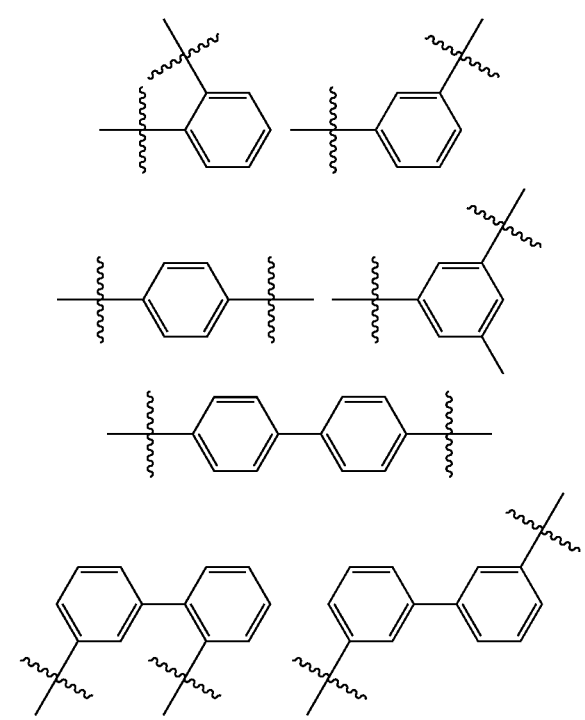

-continued
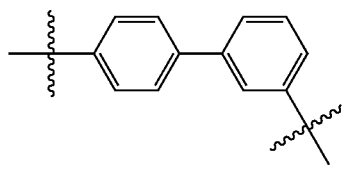
7. The compound according to claim 5, wherein Ar₁ is represented the following formulas:
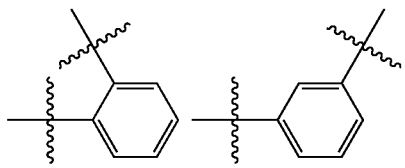
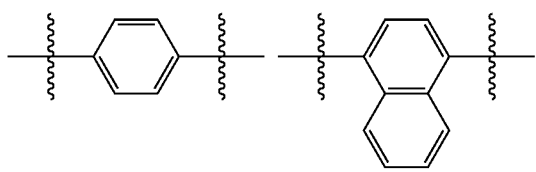
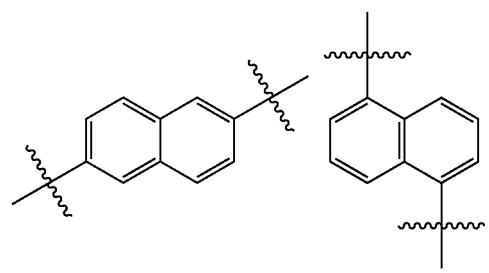
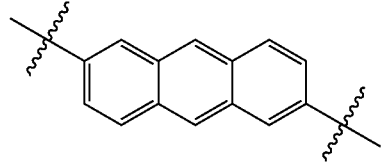
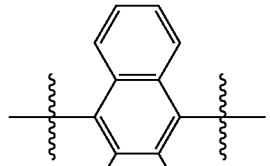
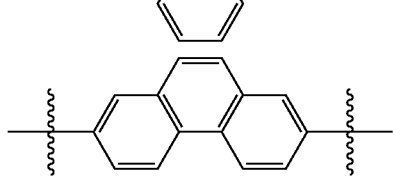
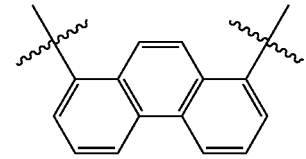
-continued
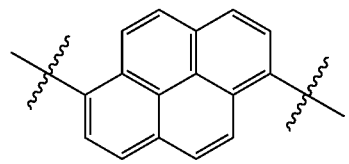
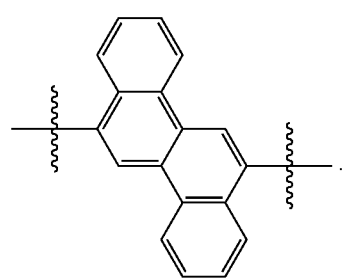
8. The compound according to claim 5, wherein Ar₂ is represented the following formulas:
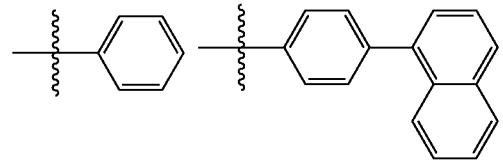
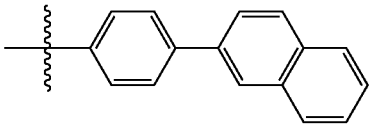
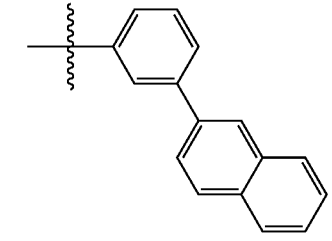
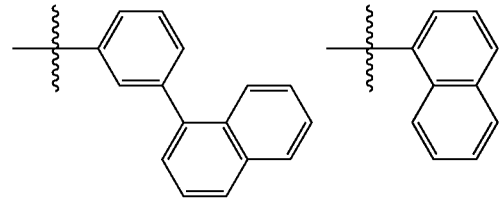
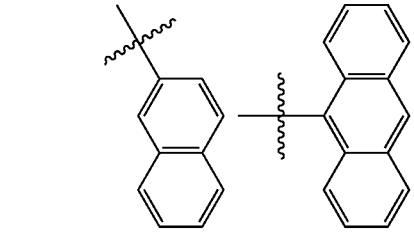
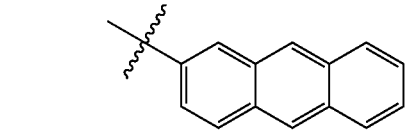

-continued

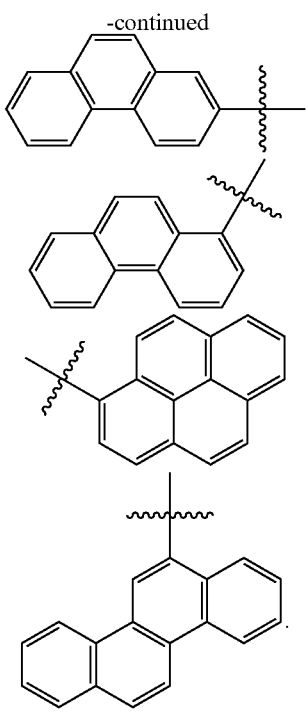

9. A organic electroluminescence device comprising a pair of electrodes consisting of a cathode and an anode, and between the pairs of electrodes comprising at least a light emitting layer, one or more layers of organic thin film layer, wherein the light emitting layer comprising the compound according to claim 1.

10. The organic electroluminescence device according to claim 9, wherein the light emitting layer comprising the compound with a general formula(I) is a host material.

11. The organic electroluminescence device according to claim 9, wherein the light emitting layer comprising the compound with a general formula(I) is a fluorescent emitter.

12. The organic electroluminescence device according to claim 9, wherein the light emitting layer emits fluorescent blue and green lights.

13. The organic electroluminescence device according to claim 9, wherein the light emitting layer emits phosphorescent green lights.

14. The organic electroluminescence device according to claim 9, wherein the device is an organic light emitting device.

15. The organic electroluminescence device according to claim 9, wherein the device is a lighting panel.

16. The organic electroluminescence device according to claim 9, wherein the device is a backlight panel.

17. A compound with one of the following formulas:

EX1

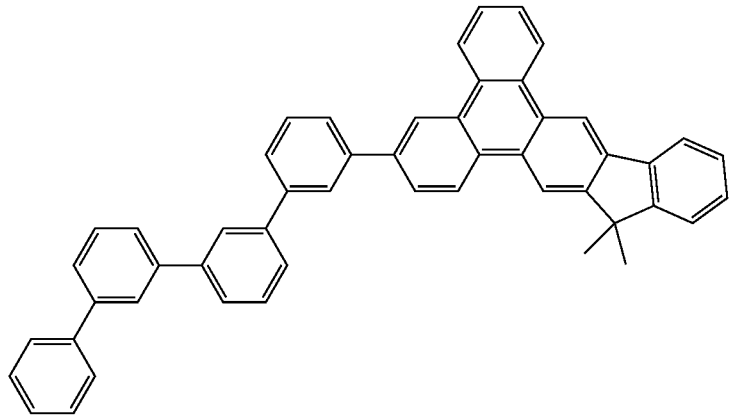

EX2

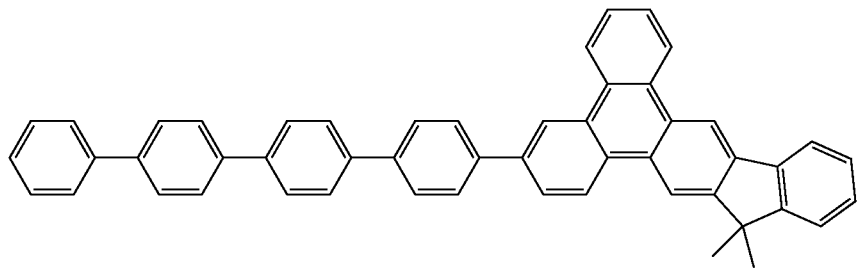

-continued
EX3
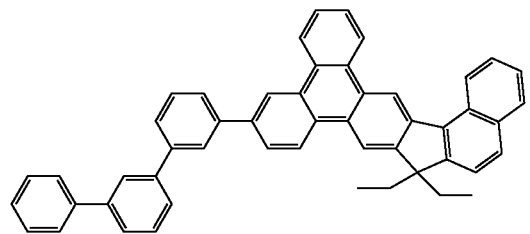
EX4
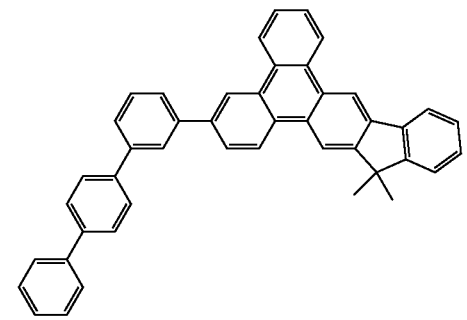
EX5
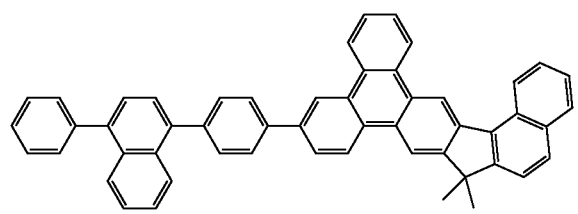
EX6
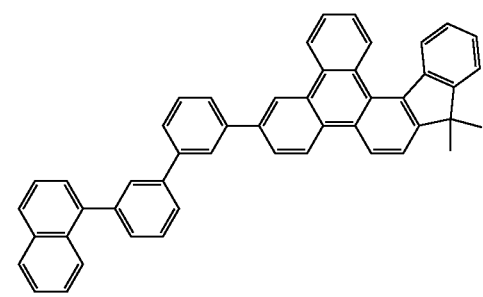
EX7
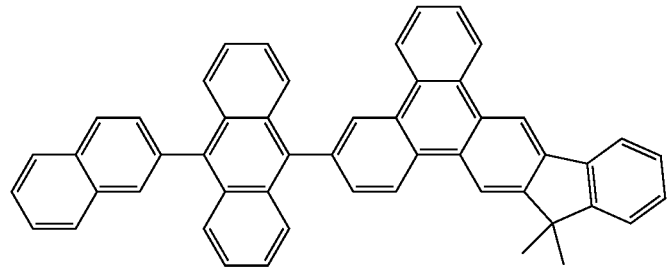
EX8
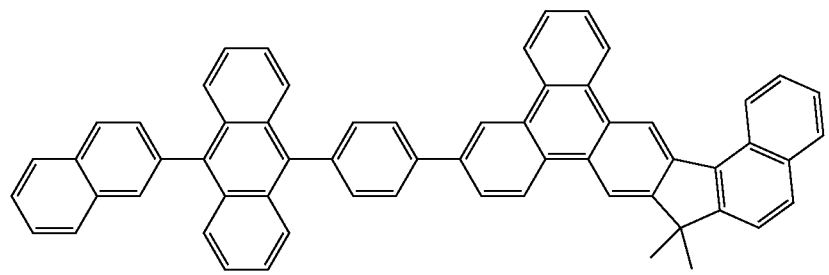
EX9
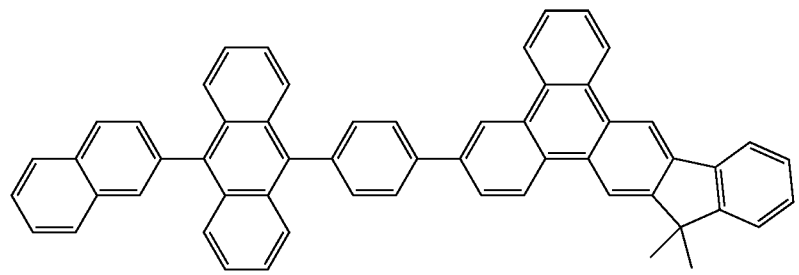

-continued
EX10
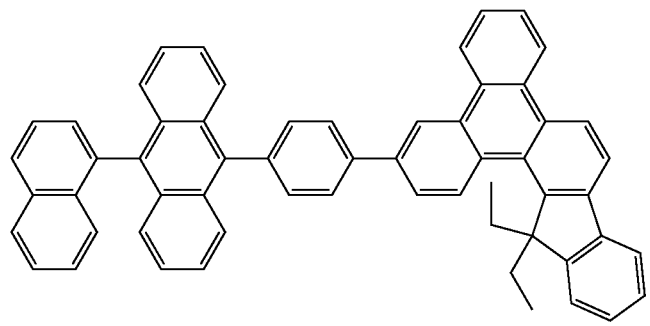
EX11
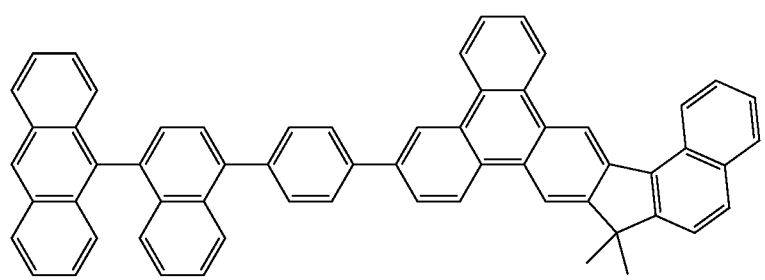
EX12
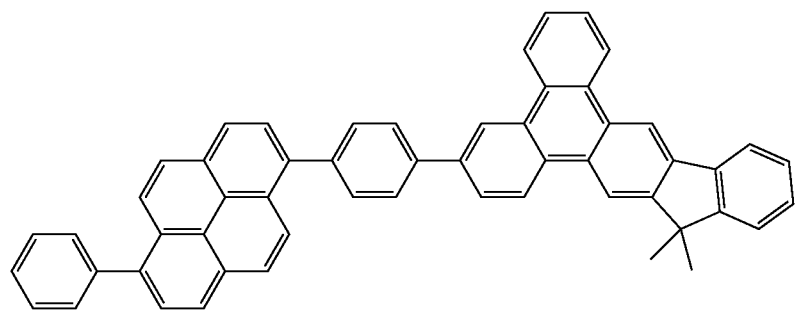
EX13
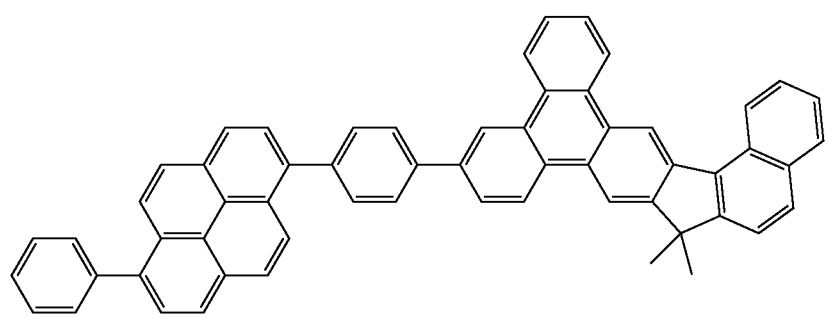
EX14
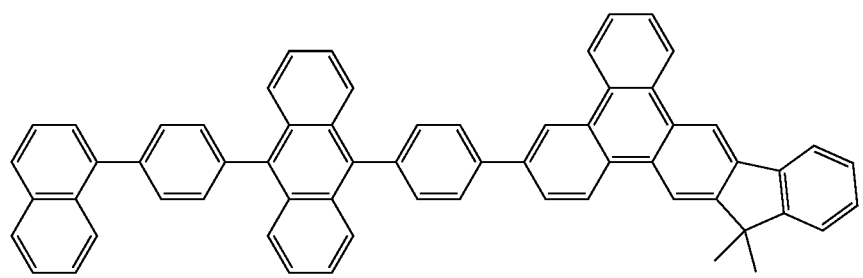

-continued
EX15
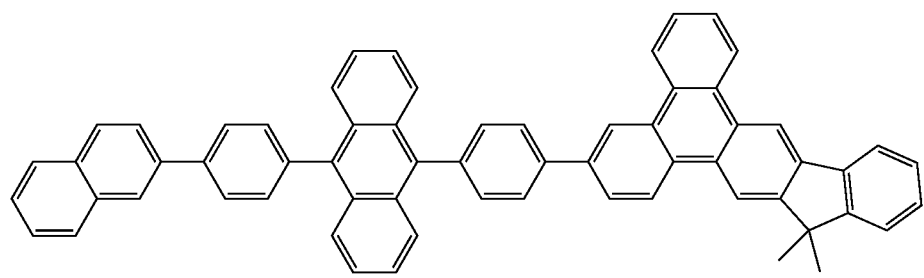
EX16
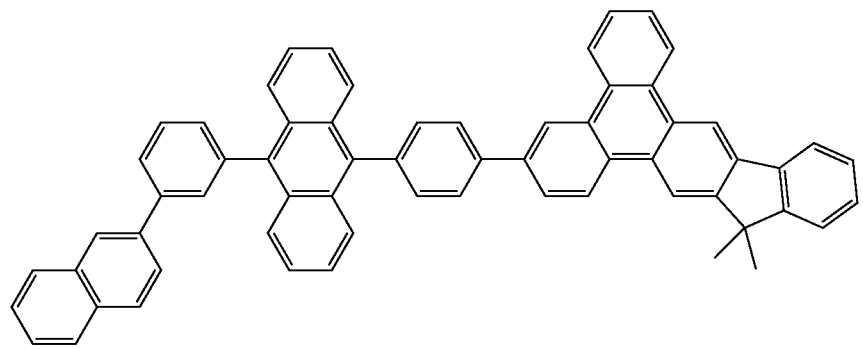
EX17
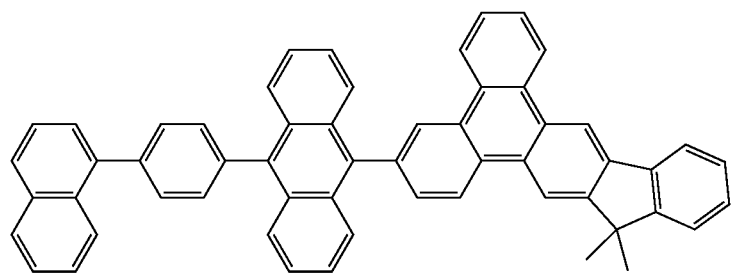
EX18
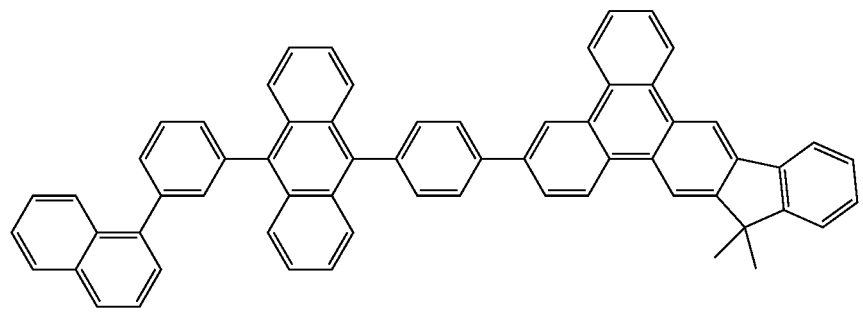
EX19
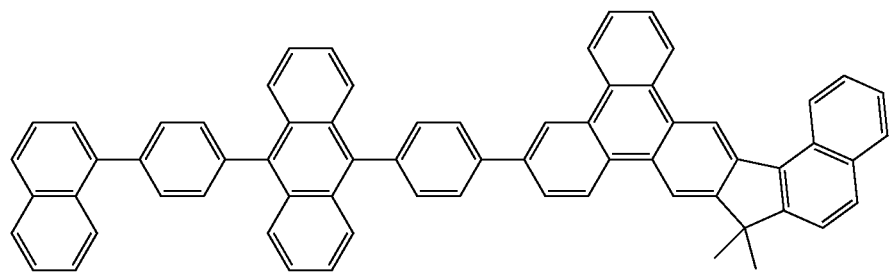

EX20
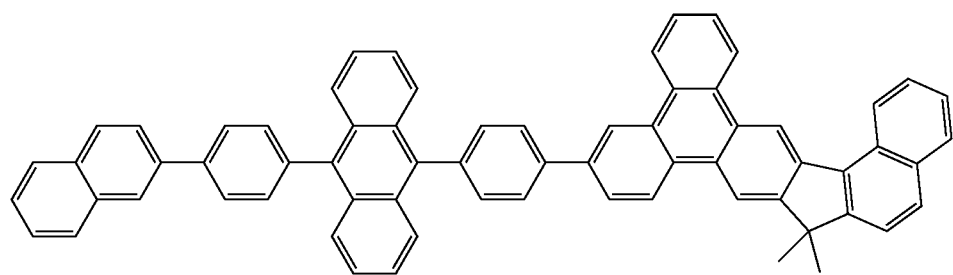
EX21
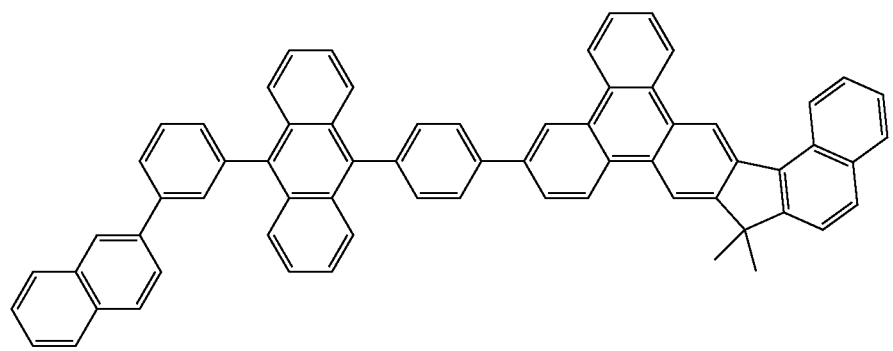
EX22
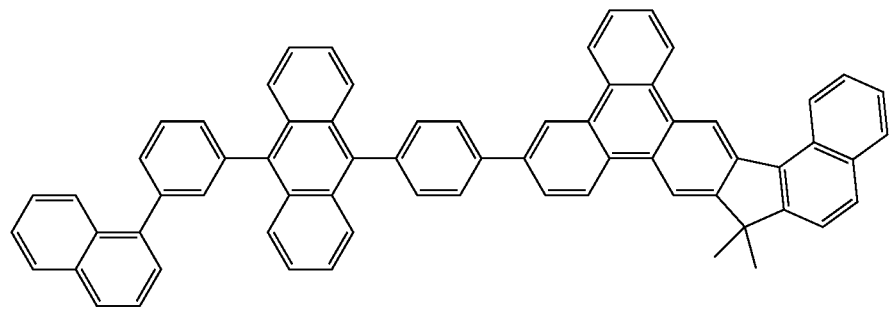
EX23
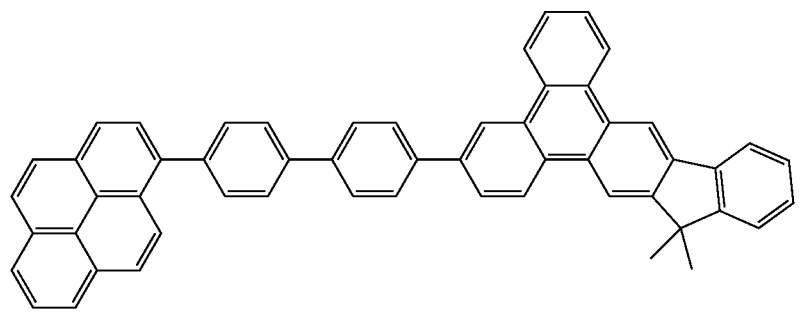
EX24
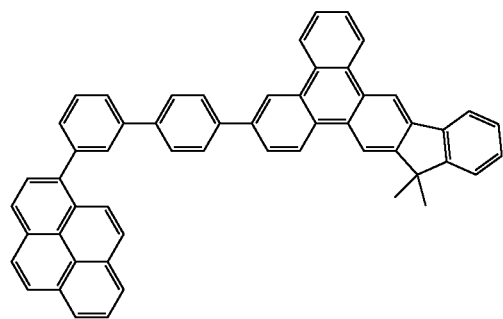
EX25
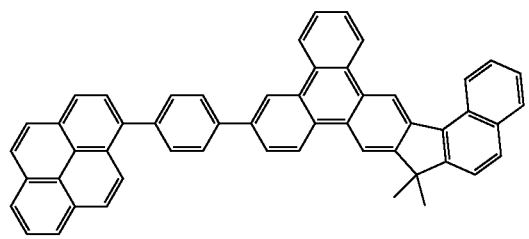

EX26
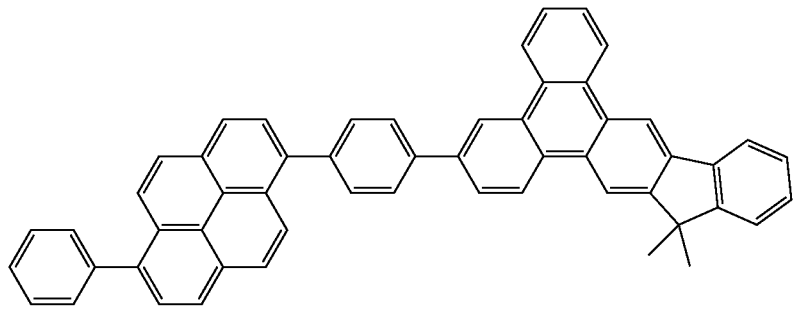
EX27
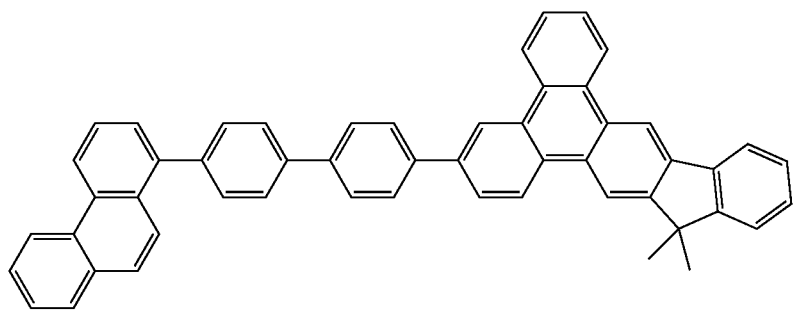
EX28
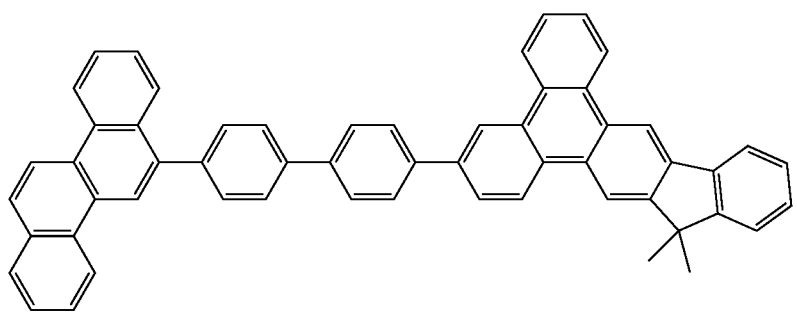
EX29
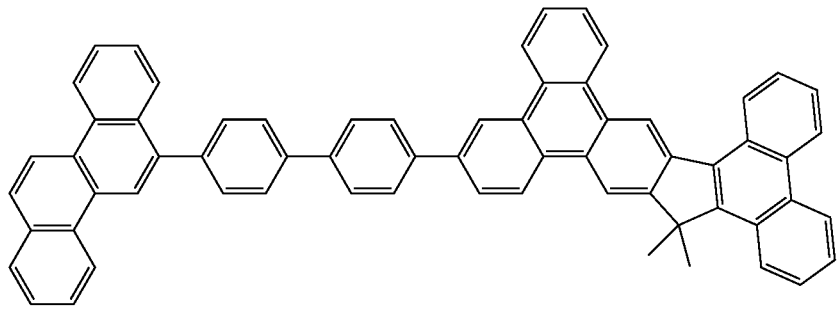
EX30
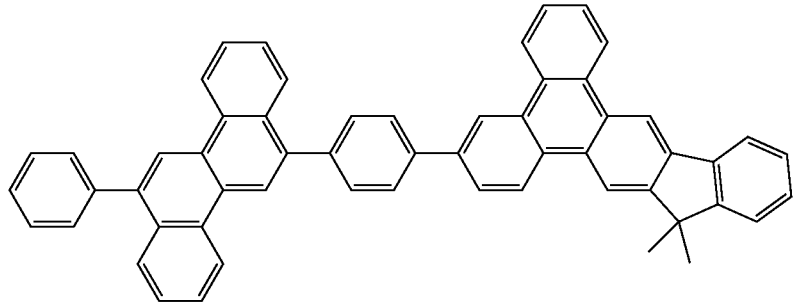

-continued
EX31
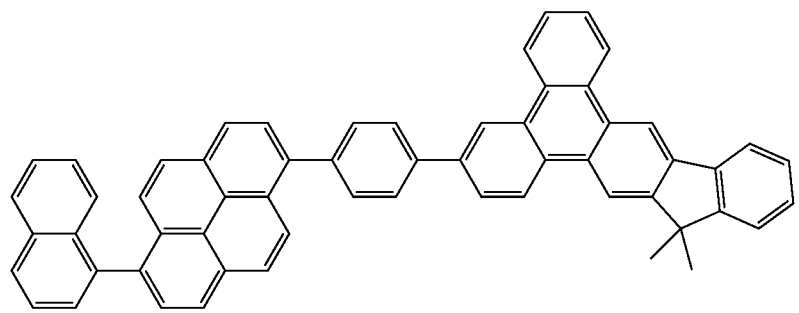
EX32
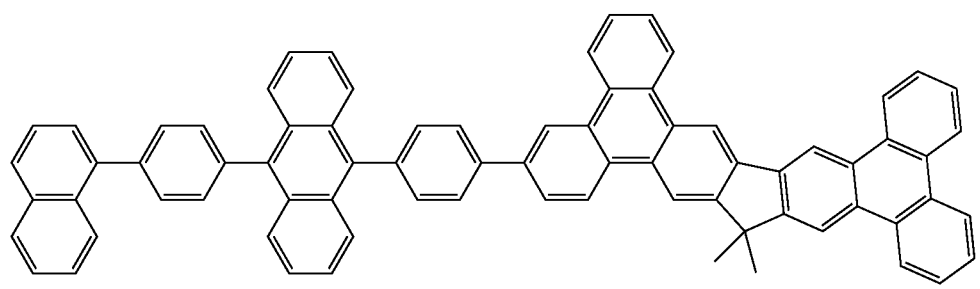
EX33
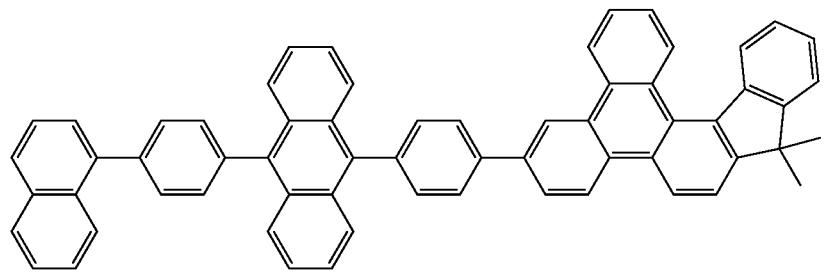
EX34
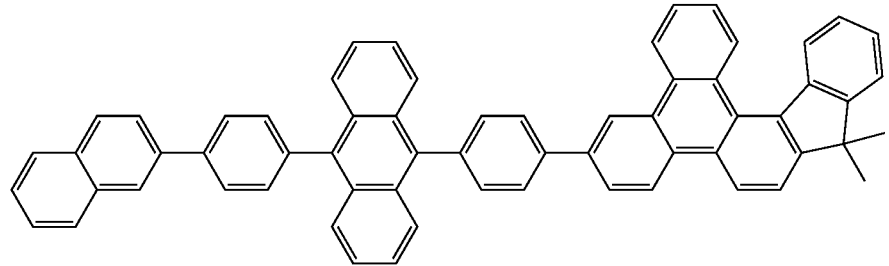
and
EX35
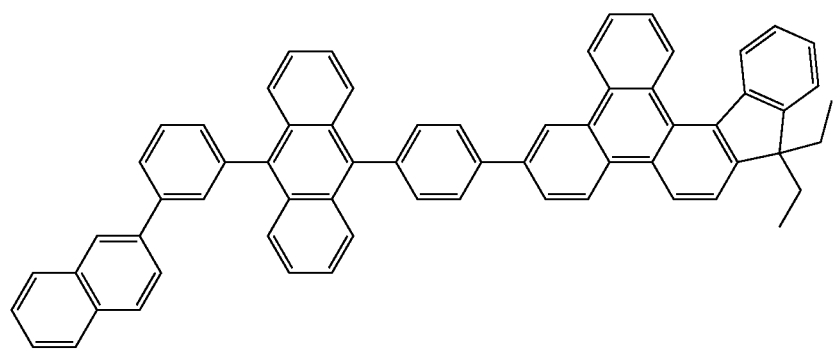
* * * * *